US010695562B2

(12) United States Patent
DeSimone et al.

(10) Patent No.: US 10,695,562 B2
(45) Date of Patent: Jun. 30, 2020

(54) INTERVENTIONAL DRUG DELIVERY SYSTEM AND ASSOCIATED METHODS

(71) Applicant: The University of North Carolina at Chapel Hill, Chapel Hill, NC (US)

(72) Inventors: Joseph DeSimone, Chapel Hill, NC (US); Mary Napier, Carrboro, NC (US); Jonathan Pillai, Chapel Hill, NC (US); James Byrne, Chapel Hill, NC (US); Lukas Miller Roush, Chapel Hill, NC (US); Jen Jen Yeh, Chapel Hill, NC (US); Matt Parrott, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1041 days.

(21) Appl. No.: 14/748,361

(22) Filed: Jun. 24, 2015

(65) Prior Publication Data
US 2016/0022985 A1 Jan. 28, 2016

Related U.S. Application Data

(63) Continuation of application No. 13/202,810, filed as application No. PCT/US2010/025416 on Feb. 25, 2010, now abandoned.
(Continued)

(51) Int. Cl.
*A61N 1/30* (2006.01)
*A61N 1/32* (2006.01)
(Continued)

(52) U.S. Cl.
CPC ............... *A61N 1/306* (2013.01); *A61N 1/00* (2013.01); *A61N 1/044* (2013.01); *A61N 1/0428* (2013.01);
(Continued)

(58) Field of Classification Search
CPC ...... A61B 18/1492; A61B 2018/00214; A61B 2018/00898; A61N 1/306; A61N 1/327;
(Continued)

(56) References Cited

U.S. PATENT DOCUMENTS 3,964,482 A 6/1976 Gerstel et al.
4,419,092 A 12/1983 Jacobsen et al.
(Continued)

FOREIGN PATENT DOCUMENTS

CA 2614572 A1 8/2006
JP H05-115562 A 5/1993
(Continued)

OTHER PUBLICATIONS

Labhasetwar et al. "Iontophoresis for modulation of cardiac drug delivery in dogs." Proc. Natl. Acad. Sci. vol. 92, pp. 2612-2616, 1995.*
(Continued)

*Primary Examiner* — Amanda Lauritzen Moher
(74) *Attorney, Agent, or Firm* — Alston & Bird LLP

(57) ABSTRACT

A delivery system for local drug delivery to a target site of internal body tissue is provided. The delivery system comprises a source electrode adapted to be positioned proximate to a target site of internal body tissue. A counter electrode is in electrical communication with the source electrode, and is configured to cooperate with the source electrode to form a localized electric field proximate to the target site. A reservoir is configured to be disposed such that the reservoir is capable of interacting with the localized electric field. The reservoir is configured to carry a cargo capable of being delivered to the target site when exposed to the localized electric field. Associated methods are also provided.

10 Claims, 43 Drawing Sheets

Related U.S. Application Data

(60) Provisional application No. 61/155,880, filed on Feb. 26, 2009.

(51) Int. Cl.
  *A61N 1/04* (2006.01)
  *A61N 1/00* (2006.01)
  *A61N 1/05* (2006.01)
  *A61B 18/00* (2006.01)
  *A61B 18/14* (2006.01)
  *A61K 9/00* (2006.01)
  *A61L 31/16* (2006.01)
  *A61N 1/36* (2006.01)

(52) U.S. Cl.
  CPC ......... *A61N 1/0444* (2013.01); *A61N 1/0448* (2013.01); *A61N 1/05* (2013.01); *A61N 1/30* (2013.01); *A61N 1/303* (2013.01); *A61N 1/325* (2013.01); *A61B 18/1492* (2013.01); *A61B 2018/00214* (2013.01); *A61B 2018/00898* (2013.01); *A61K 9/0002* (2013.01); *A61K 9/0009* (2013.01); *A61K 9/0024* (2013.01); *A61L 31/16* (2013.01); *A61N 1/0507* (2013.01); *A61N 1/327* (2013.01); *A61N 1/36002* (2017.08)

(58) Field of Classification Search
  CPC . A61N 1/303; A61N 1/30; A61N 1/05; A61N 1/0448; A61N 1/0444; A61N 1/044; A61N 1/00; A61N 1/0428; A61N 1/325; A61N 1/36002; A61N 1/0507; A61L 31/16; A61K 9/0024; A61K 9/0002; A61K 9/0009
  See application file for complete search history.

(56) References Cited

U.S. PATENT DOCUMENTS

| | | |
|---|---|---|
| 4,519,938 A | 5/1985 | Papir |
| 4,722,726 A | 2/1988 | Sanderson et al. |
| 4,731,049 A | 3/1988 | Parsi |
| 4,744,787 A | 5/1988 | Phipps et al. |
| 4,747,819 A | 5/1988 | Phipps et al. |
| 4,915,685 A | 4/1990 | Petelenz et al. |
| 4,979,938 A | 12/1990 | Stephen et al. |
| 5,037,380 A | 8/1991 | Jacobsen et al. |
| 5,057,072 A | 10/1991 | Phipps |
| 5,080,646 A | 1/1992 | Theeuwes et al. |
| 5,084,006 A | 1/1992 | Lew et al. |
| 5,084,008 A | 1/1992 | Phipps |
| 5,087,242 A | 2/1992 | Petelenz et al. |
| 5,087,243 A * | 2/1992 | Avitall ............... A61N 1/3956 604/20 |
| 5,135,477 A | 8/1992 | Untereker et al. |
| 5,162,043 A | 11/1992 | Lew et al. |
| 5,169,383 A | 12/1992 | Gyory et al. |
| 5,236,412 A | 8/1993 | Lloyd et al. |
| 5,248,295 A | 9/1993 | Jacobsen et al. |
| 5,281,287 A | 1/1994 | Lloyd et al. |
| 5,282,785 A | 2/1994 | Shapland et al. |
| 5,320,597 A | 6/1994 | Sage, Jr. et al. |
| 5,320,598 A | 6/1994 | Haak et al. |
| 5,322,502 A | 6/1994 | Theeuwes et al. |
| 5,326,341 A | 7/1994 | Lew et al. |
| 5,328,455 A | 7/1994 | Lloyd et al. |
| 5,374,241 A | 12/1994 | Lloyd et al. |
| 5,374,242 A | 12/1994 | Haak et al. |
| 5,385,543 A | 1/1995 | Haak et al. |
| 5,395,310 A | 3/1995 | Untereker et al. |
| 5,405,317 A | 4/1995 | Myers et al. |
| 5,415,629 A | 5/1995 | Henley |
| 5,458,569 A | 10/1995 | Kirk, III et al. |
| 5,492,547 A | 2/1996 | Johnson |
| 5,496,266 A | 3/1996 | Haak et al. |
| 5,499,971 A | 3/1996 | Shapland et al. |
| 5,503,632 A | 4/1996 | Haak |
| 5,505,700 A | 4/1996 | Leone et al. |
| 5,533,972 A | 7/1996 | Gyory et al. |
| 5,533,995 A | 7/1996 | Corish et al. |
| 5,538,503 A | 7/1996 | Henley |
| 5,540,669 A | 7/1996 | Sage, Jr. et al. |
| 5,543,098 A | 8/1996 | Myers et al. |
| 5,558,632 A | 9/1996 | Lloyd et al. |
| 5,573,668 A | 11/1996 | Grosh et al. |
| 5,582,587 A | 12/1996 | Gyory et al. |
| 5,637,084 A | 6/1997 | Kontturi et al. |
| 5,645,526 A | 7/1997 | Flower |
| 5,645,527 A | 7/1997 | Beck |
| 5,647,844 A | 7/1997 | Haak et al. |
| 5,658,247 A | 8/1997 | Henley |
| 5,667,487 A | 9/1997 | Henley |
| 5,668,170 A | 9/1997 | Gyory |
| 5,693,024 A | 12/1997 | Flower |
| 5,704,908 A | 1/1998 | Hofmann et al. |
| 5,711,761 A | 1/1998 | Untereker et al. |
| 5,713,846 A | 2/1998 | Bernhard et al. |
| 5,730,716 A | 3/1998 | Beck et al. |
| 5,788,666 A | 8/1998 | Atanasoska |
| 5,795,321 A | 8/1998 | McArthur et al. |
| 5,830,175 A | 11/1998 | Flower |
| 5,840,056 A | 11/1998 | Atanasoska |
| 5,846,217 A | 12/1998 | Beck et al. |
| 5,857,993 A | 1/1999 | Atanasoska et al. |
| 5,857,994 A | 1/1999 | Flower |
| 5,860,957 A | 1/1999 | Jacobsen et al. |
| 5,871,460 A | 2/1999 | Phipps et al. |
| 5,871,461 A | 2/1999 | Atanasoska et al. |
| 5,876,368 A | 3/1999 | Flower |
| 5,895,369 A | 4/1999 | Flower |
| 5,919,156 A | 7/1999 | Stropkay et al. |
| 5,925,066 A | 7/1999 | Kroll et al. |
| 5,941,843 A | 8/1999 | Atanasoska et al. |
| 5,954,684 A | 9/1999 | Flower et al. |
| 5,983,133 A | 11/1999 | Garde et al. |
| 5,991,655 A | 11/1999 | Gross et al. |
| 5,993,435 A | 11/1999 | Haak et al. |
| 6,009,344 A | 12/1999 | Flower et al. |
| 6,018,680 A | 1/2000 | Flower |
| 6,029,083 A | 2/2000 | Flower et al. |
| 6,048,545 A | 4/2000 | Keller et al. |
| 6,049,733 A | 4/2000 | Phipps et al. |
| 6,062,915 A | 5/2000 | Costello et al. |
| 6,064,908 A | 5/2000 | Muller et al. |
| 6,103,078 A | 8/2000 | Hitchems et al. |
| 6,132,755 A | 10/2000 | Eicher et al. |
| 6,165,155 A | 12/2000 | Jacobsen et al. |
| 6,167,302 A | 12/2000 | Millot |
| 6,169,920 B1 | 1/2001 | Haak et al. |
| 6,185,453 B1 | 2/2001 | Hussain et al. |
| 6,219,577 B1 | 4/2001 | Brown, III et al. |
| 6,223,075 B1 | 4/2001 | Beck et al. |
| 6,256,533 B1 | 7/2001 | Yuzhakov et al. |
| 6,258,276 B1 | 7/2001 | Mika et al. |
| 6,287,484 B1 | 9/2001 | Hausslein et al. |
| 6,314,317 B1 | 11/2001 | Willis |
| 6,319,240 B1 | 11/2001 | Beck |
| 6,350,259 B1 | 2/2002 | Sage, Jr. et al. |
| 6,377,847 B1 | 4/2002 | Keusch et al. |
| 6,377,848 B1 | 4/2002 | Garde et al. |
| 6,385,488 B1 | 5/2002 | Flower et al. |
| 6,391,015 B1 | 5/2002 | Millot |
| 6,394,994 B1 | 5/2002 | Vilambi et al. |
| 6,424,862 B1 | 7/2002 | Brown, III et al. |
| 6,477,411 B1 | 11/2002 | Beck |
| 6,488,428 B1 | 12/2002 | Fischer |
| 6,490,482 B2 | 12/2002 | Mori et al. |
| 6,503,231 B1 | 1/2003 | Prausnitz et al. |
| 6,539,251 B2 | 3/2003 | Beck et al. |
| 6,546,283 B1 | 4/2003 | Beck et al. |
| 6,546,284 B2 | 4/2003 | Plummer |
| 6,553,255 B1 | 4/2003 | Miller et al. |

(56) References Cited

U.S. PATENT DOCUMENTS

| | | | |
|---|---|---|---|
| 6,576,712 B2 | 6/2003 | Feldstein et al. |
| 6,579,276 B2 | 6/2003 | Lloyd et al. |
| 6,587,718 B2 | 7/2003 | Talpade |
| 6,611,707 B1 | 8/2003 | Prausnitz et al. |
| 6,625,486 B2 | 9/2003 | Lundkvist et al. |
| 6,635,045 B2 | 10/2003 | Keusch et al. |
| 6,662,044 B2 | 12/2003 | Crawford et al. |
| 6,678,555 B2 | 1/2004 | Flower et al. |
| 6,687,536 B1 | 2/2004 | Beck et al. |
| 6,697,668 B2 | 2/2004 | Parkinson et al. |
| 6,728,573 B1 | 4/2004 | Beck et al. |
| 6,731,977 B2 | 5/2004 | Beck |
| 6,731,987 B1 | 5/2004 | McAdams et al. |
| 6,745,071 B1 | 6/2004 | Anderson et al. |
| 6,775,569 B2 | 8/2004 | Mori et al. |
| 6,823,202 B2 | 11/2004 | Hause, Jr. |
| 6,858,018 B1 | 2/2005 | Green et al. |
| 6,862,473 B2 | 3/2005 | Keusch et al. |
| 6,953,446 B2 | 10/2005 | Fischer |
| 6,978,172 B2 | 12/2005 | Mori et al. |
| 7,018,345 B2 | 3/2006 | Mori et al. |
| 7,031,768 B2 | 4/2006 | Anderson et al. |
| 7,043,297 B2 | 5/2006 | Keusch et al. |
| 7,137,965 B2 | 11/2006 | Fischer et al. |
| 7,252,655 B2 | 8/2007 | Beck et al. |
| 7,349,733 B2 * | 3/2008 | Joshi | A61N 1/0428 604/20 |
| 2001/0001816 A1 | 5/2001 | Feiring |
| 2001/0039393 A1 | 11/2001 | Mori et al. |
| 2002/0037977 A1 | 3/2002 | Feldstein et al. |
| 2002/0055703 A1 | 5/2002 | Mori et al. |
| 2002/0099320 A1 | 7/2002 | Beck |
| 2002/0099321 A1 | 7/2002 | Plummer |
| 2002/0151866 A1 | 10/2002 | Lundkvist et al. |
| 2002/0188282 A1 * | 12/2002 | Greenberg | A61F 9/0017 604/890.1 |
| 2002/0193754 A1 | 12/2002 | Cho |
| 2003/0040696 A1 | 2/2003 | Mori et al. |
| 2003/0055405 A1 | 3/2003 | Keusch et al. |
| 2003/0060797 A1 | 3/2003 | Fischer |
| 2003/0060798 A1 | 3/2003 | Fischer et al. |
| 2003/0067358 A1 | 4/2003 | Flower et al. |
| 2003/0088204 A1 * | 5/2003 | Joshi | A61N 1/0428 604/20 |
| 2003/0097090 A1 | 5/2003 | Mori et al. |
| 2004/0167459 A1 | 8/2004 | Higuchi et al. |
| 2004/0182704 A1 * | 9/2004 | Daunert | A61K 9/0024 204/405 |
| 2004/0220511 A1 | 11/2004 | Scott et al. |
| 2004/0242770 A1 | 12/2004 | Feldstein et al. |
| 2004/0248320 A1 * | 12/2004 | Santini, Jr. | A61K 9/0009 436/174 |
| 2005/0070840 A1 | 3/2005 | Matsumura et al. |
| 2005/0131338 A1 | 6/2005 | Keusch et al. |
| 2005/0159698 A1 | 7/2005 | Keusch et al. |
| 2005/0159699 A1 | 7/2005 | Keusch et al. |
| 2005/0159700 A1 | 7/2005 | Keusch et al. |
| 2005/0171575 A1 | 8/2005 | Dev et al. |
| 2006/0047261 A1 | 3/2006 | Joshi |
| 2006/0095001 A1 | 5/2006 | Matsumura et al. |
| 2006/0116628 A1 | 6/2006 | Matsumura et al. |
| 2006/0129085 A1 | 6/2006 | Tanioka et al. |
| 2006/0135906 A1 | 6/2006 | Matsumura et al. |
| 2006/0173401 A1 | 8/2006 | Tanioka et al. |
| 2006/0184092 A1 * | 8/2006 | Atanasoska | A61N 1/325 604/20 |
| 2006/0217654 A1 | 9/2006 | Matsumura et al. |
| 2006/0276742 A1 | 12/2006 | Matsumura et al. |
| 2007/0027426 A1 | 2/2007 | Matsumura et al. |
| 2007/0060859 A1 | 3/2007 | Kanamura et al. |
| 2007/0060860 A1 | 3/2007 | Nakayama et al. |
| 2007/0066930 A1 | 3/2007 | Tanioka et al. |
| 2007/0066931 A1 | 3/2007 | Kanamura et al. |
| 2007/0066932 A1 | 3/2007 | Akiyama et al. |
| 2007/0073212 A1 | 3/2007 | Matsumura |
| 2007/0078375 A1 | 4/2007 | Smith |
| 2007/0083147 A1 | 4/2007 | Smith |
| 2007/0083185 A1 | 4/2007 | Carter |
| 2007/0083186 A1 | 4/2007 | Carter et al. |
| 2007/0088332 A1 | 4/2007 | Akiyama et al. |
| 2007/0093787 A1 | 4/2007 | Smith |
| 2007/0100275 A1 | 5/2007 | Fischer et al. |
| 2007/0100317 A1 | 5/2007 | Fischer et al. |
| 2007/0106143 A1 | 5/2007 | Flaherty |
| 2007/0110810 A1 | 5/2007 | Smith |
| 2007/0112294 A1 | 5/2007 | Akiyama et al. |
| 2007/0135754 A1 | 6/2007 | Akiyama et al. |
| 2007/0225634 A1 | 9/2007 | Ferren et al. |
| 2007/0232985 A1 | 10/2007 | Sirkar et al. |
| 2008/0003260 A1 | 1/2008 | Warren et al. |
| 2008/0009501 A1 | 1/2008 | Warren et al. |
| 2008/0063703 A1 | 3/2008 | Gross et al. |
| 2008/0065002 A1 | 3/2008 | Lobl et al. |
| 2008/0114282 A1 * | 5/2008 | Carter | A61N 1/044 604/20 |
| 2008/0131483 A1 | 6/2008 | Abdulrazik |
| 2008/0154230 A1 | 6/2008 | Subramony et al. |
| 2008/0175895 A1 | 7/2008 | Kogure et al. |
| 2008/0214987 A1 | 9/2008 | Xu |
| 2008/0226687 A1 | 9/2008 | Cormier et al. |
| 2008/0262412 A1 | 10/2008 | Atanasoska et al. |
| 2008/0275016 A1 | 11/2008 | Arbiser |
| 2008/0287866 A1 | 11/2008 | Heller |
| 2009/0024075 A1 | 1/2009 | Schroeppel et al. |
| 2009/0043276 A1 * | 2/2009 | Weber | A61F 2/88 604/502 |
| 2009/0263468 A1 * | 10/2009 | McAnulty | A61K 47/42 424/443 |
| 2010/0023004 A1 | 1/2010 | Francischelli et al. |
| 2010/0331760 A1 * | 12/2010 | Atanasoska | A61K 9/0009 604/20 |
| 2014/0248320 A1 | 9/2014 | Tsai |
| 2018/0036522 A1 * | 2/2018 | Davey | A61M 5/14276 |

FOREIGN PATENT DOCUMENTS

| | | |
|---|---|---|
| JP | 2001-506172 A | 5/2001 |
| JP | P3372250 B2 | 11/2002 |
| WO | WO 98/41655 A1 | 9/1998 |
| WO | WO 99/04850 A1 | 2/1999 |
| WO | WO 99/17837 A1 | 4/1999 |
| WO | WO 99/32661 A1 | 7/1999 |
| WO | WO 99/52424 A1 | 10/1999 |
| WO | WO 01/27325 A1 | 4/2001 |
| WO | WO 01/49104 A2 | 7/2001 |
| WO | WO 2005/101466 A2 | 10/2005 |
| WO | WO 2006/044795 A2 | 4/2006 |
| WO | WO 2007/024323 A2 | 3/2007 |
| WO | WO 2007/030698 A2 | 3/2007 |
| WO | WO 2007/111365 A1 | 4/2007 |
| WO | WO 2007/094829 A2 | 8/2007 |
| WO | WO 2008/013952 A2 | 1/2008 |
| WO | WO 2008/124634 A1 | 10/2008 |

OTHER PUBLICATIONS

Schwendeman et al. "Modulated drug release using iontophoresis through heterogeneous cation-exchange membranes. 2. Influence of cation-exchanger content on membrane resistance." Journal of Pharmaceutical Sciences 83(10), pp. 1482-1494, 1994.*

Henley. Transcutaneous drug delivery: Iontophoresis, phonophoresis. Physical and Rehabilitation Medicine, 2, pp. 139-151, 1991.*

Sieg et al. Diagnostic and therapeutic applications of iontophoresis. J Drug Target, 17, pp. 690-700, 2009.*

Office Action for Canadian Application No. 2,790,324 dated Feb. 5, 2018, 5 pages.

Office Action for Indian Application No. 3968/KOLNP/2011 dated Oct. 24, 2018, 5 pages.

Kirstein et al., "High-performance liquid chromatographic method for the determination of gemcitabine and 2',2'-difluorodeoxyuridine

(56) References Cited

OTHER PUBLICATIONS in plasma and tissue culture media." Journal of Chromatography B, 835 (2006), pp. 136-142.
Olive et al., "Inhibition of Hedgehog Signaling Enhances Delivery of Chemotherapy in a Mouse Model of Pancreatic Cancer." Science, vol. 324, Jun. 12, 2009, pp. 1457-1461.
Communication from European Patent Office from European Application No. 10707731.5 dated Mar. 13, 2015.
Office Action for Canadian Application No. 2,790,324 dated Mar. 10, 2016, 6 pages.
Office Action for European Application No. 10 707 731.5 dated Jul. 15, 2016, 4 pages.
Patent Examination Report No. 1 for Australian Patent Application No. 2010217957 dated Nov. 7, 2013, 3 pages.
Patent Examination Report No. 2 for Australian Patent Application No. 2010217957 dated Jan. 15, 2015, 3 pages.
Office Action for Chinese Application No. 201080018560.X dated Jul. 26, 2013, 17 pages.
Office Action for Chinese Application No. 201080018560.X dated Mar. 18, 2014, 15 pages.
Office Action for Chinese Application No. 201080018560.X dated Feb. 2, 2015, 7 pages.
Office Action for Japanese Application No. 2011-552156 dated May 26, 2014, 6 pages.
Office Action for Korean Application No. 10-2011-7022469 dated Mar. 14, 2016, 5 pages.
Office Action for Canadian Application No. 2,790,324 dated Mar. 8, 2017, 5 pages.
Molokhia, S. A. et al., *Iontophoretic Transport Across a Multiple Membrane System*, J. Pharm Sci. 97(1)(dated Jan. 2008) 490-505.
Abla, N. et al., *Effect of Charge and Molecular Weight on Transdermal Peptide Delivery by Iontophoresis*, Pharm Res 22 (2005) 2069-78.
Alvarez-Figueroa, M. J. et al., *Passive and Iontophoretic Transdermal Penetration of Methotrexate*, Int J Pharm 212 (2001) 101-7.
Banga, A. K. et al., *Iontophoretic Delivery of Drugs: Fundamentals, Developments and Biomedical Applications*, Journal of Controlled Release, 7 (1988) 1-24.
Bardeesy, N. et al., *Pancreatic Cancer Biology and Genetics*, Nature Reviews, 2002, vol. 2, pp. 897-909.
Chang, B. K. et al., *A Pilot Study Iontophoretic Cisplatin Chemotherapy of Basal and Squamous Cell Carcinomas of the Skin*, Arch Dermatol 129 (1993) 425-7.
Chang, K. J. et al., *Endoscopic Ultrasound Delivery of an Antitumor Agent to Treat a Case of Pancreatic Cancer*, Nature Clinical Practice Gastroenterology & Hepatology 5 (2008) 107-111.
Di Stasi, S. M. et al., *Electromotive Delivery of Mitomycin C into Human Bladder Wall*, Cancer Research, vol. 67 (1997) pp. 875-880.
Di Stasi, S. M. et al., *Sequential BCG and electromotive mitomycin versus BCG alone for high-risk superficial bladder cancer: a randomized controlled trial*, http.//oncology.thelancet.com, vol. 7 (2006) pp. 43-51.
Di Stasi, S. M. et al., *Updates in Intravesical Electromotive Drug Administration® of Mitomycin-C for Non-Muscle Invasive Bladder Cancer*, World J Urol 27 (2009) 325-330.
Di Stasi, S. M. et al., *Electromotive Versus Passive Diffusion of Mitomycin C Into Human Bladder Wall: Concentration-Depth Profiles Studies*, Cancer Res 59 (1999) 4912-4918.
Dixit, N. et al., *Iontophoresis—An Approach for Controlled Drug Delivery: A Review*, Current Drug Delivery, 4 (2007), 1-10.
Eliarrat-Binstock, E. et al., *Charged Nanoparticles Delivery to the Eye Using Hydrogel Iontophoresis*, J Control Rel 126 (2008) 156-161.
Fernandez-Ortiz, A. et al., *A New Approach for Local Intravascular Drug Delivery. Iontophoretic Balloon*, Circulation 89(4) (1994), pp. 1518-1522.
Gazelius B., *Iontophoresis—Theory*, Periflux Systems, Innovations in Microvascular Diagnosis, PERIMED, (1999), pp. 1-7.
Guy, R. H. et al., *Iontophoresis: Electrorepulsion and Electroosmosis*, J Control Rel 64 (2000) 129-32.

Hodgkin, D. D. et al., *Electrophysiologic Characteristics of a Pulse Drug-Delivery System in Coronary Arteries*, J of Cardiovascular Pharmacology 29 (1997) 39-44.
Kalia, Y. N. et al., *Iontophoretic Drug Delivery*, Adv Drug Deliv Rev 56 (2004) 619-58.
Kasha et al. *A Review of Patent Literature for Iontophoretic Delivery and Devices*, Recent Patents on Drug Delivery & Formulation, vol. 2 (2008), pp. 41-50.
Kelly, J. Y. et al., *Shape-Specific, Monodisperse Nano-Molding of Protein Particles*, J Am Chem Soc 130 (2008) 5438-9.
Li, S. K. et al., *Influence of Asymmetric Donor-Receiver Ion Concentration Upon Transscleral Iontophoretic Transport*, J Pharm Sci 94 (2005) 847-60.
Lopez, R. F. et al., *Iontophoretic Delivery of 5-Aminolevulinic Acid (ALA): Effect of pH*, Pharm Res 18 (2001) 311-5.
Marro, D. et al., *Optimizing Iontophoretic Drug Delivery: Identification and Distribution of the Charge-Carrying Species*, Pharm Res 18 (2001) 1709-13.
Matsumoto, K. et al., *Endoscopic Ultrasound-guided Ethanol Injection in the Pancreas in a Porcine Model: A Preliminary Study*, Journal of Gastroenterology and Hepatology 23(2008) pp. e1-e6.
Merino, V. et al., *Electrorepulsion Versus Electroosmosis: Effect of pH on the Iontophoretic Flux of 5-Fluorouracil*, Pharmaceutical Research, vol. 16, No. 5 (1999), 758-761.
Minchinton, A. I. et al., *Drug Penetration in Solid Tumours*, Nat Rev Cancer 6 (2006) 583-92.
Patane, M. et al., *Iontophoretic Delivery of PRINT Nanoparticles Using the EyeGate II Device*, Controlled Release Society Meeting, 2008.
Phipps, J. B. et al., *Iontophoretic Delivery of Model Inorganic and Drug Ions*, J Pharm Sci 78 (1989) 365-9.
Phipps, J. B. et al., *Iontophoresis*, Encyclopedia of Pharmaceutical Technology, Marcel Dekker (2002) 1573-1587.
Robinson, K. A. et al., *Pharmacokinetics and Tissue Localization of Antisense Oligonucleotides in Balloon-Injured Pig Coronary Arteries After Local Delivery With an Iontophoretic Balloon Catheter*, Catheterization and Cardiovascular Diagnosis, 41 (1997), pp. 354-359.
Rolland, J. P. et al., *Direct Fabrication and Harvesting of Monodisperse, Shape-Specific Nanobiomaterials*, J Am Chem Soc 127 (2005) 10096-100.
Semalty, A. et al., *Iontophoretic Drug Delivery System: A Review*, Technology and Health Care, 15(4) (2007), pp. 237-245.
Singh, J. et al., *Transdermal Iontophoresis: Effect of Penetration Enhancer and Iontophoresis on Drug Transport and Surface Characteristics of Human Epidermis*, Curr Probl Dermatol 22 (1995) 179-83.
Smith, K. J. et al., *Iontophoresis of Vinblastine Into Normal Skin and for Treatment of Kaposi's Sarcoma in Human Immunodeficiency Virus-Positive Patients*, The Military Medical Consortium for Applied Retroviral Research, Arch Dermatol 128 (1992) 1365-70.
Von Wichert, G. et al., *Palliative Treatment of Pancreatic Cancer*, J Dig Dis 9 (2008) 1-7.
Welch, M. L. et al., *5-fluorouracil Iontophoretic Therapy for Bowen's Disease*, J Am Acad Dermatol 36 (1997) 956-8.
*World Cancer Report 2008*, International Agency for Research on Cancer (2008).
ActivaTek Inc.—Scientific Evidence [online] [retrieved Feb. 6, 2008]. Retrieved from the Internet: <URL: http://www.activatekinc.com/evidence.html>. 1 page.
ActivaTek Inc.—Iontophoresis [online] [retrieved Feb. 6, 2008]. Retrieved from the Internet: <URL: http://www.activatekinc.com/iontophoresis.html>. 1 page.
Drug Delivery Technology—Article Index [online] [retrieved Feb. 6, 2008]. Retrieved from the Internet: <URL: http://www.drugdeliverytech.com/cgi-bin/articles.cgi?idArticle=66>. 4 pages.
*Electrophysiologic Characteristics of a Pulsed Iontophoretic. . .* [online] [retrieved Nov. 18, 2010]. Retrieved from the Internet: <URL: http://journals.lww.com/cardiovascularpharm/fulltext/1997/01000/electr. . . >. 8 pages.
Iontophoretic Delivery of Drugs—Dr. Mary Korula [online] [retrieved Feb. 6, 2008]. Retrieved from the Internet: <URL: http://www.theiaforum.org/april2004.htm>. 12 pages.

(56) References Cited

OTHER PUBLICATIONS

Iontophoretic drug delivery [online] [retrieved Feb. 6, 2008]. Retrieved from the Internet: <URL: http://www.aapspharmaceutica.com/search/view.asp?ID=51476>. 1 page.
International Preliminary Report on Patentability for Application No. PCT/US2009/035070 dated Sep. 10, 2010.
International Search Report and Written Opinion for Application No. PCT/US2010/025416 dated Jul. 20, 2010.
International Search Report for Application No. PCT/US2009/035070 dated Jun. 3, 2009.
Communication for European Patent Application No. 09715607.9 dated Jan. 21, 2011.
Communication for European Application No. 04 753 645.3 dated Jan. 22, 2010.
Communication from European Patent Office from European Application No. 10707731.5 dated Aug. 6, 2012.
International Search Report and Written Opinion for Application No. PCT/US2009/035070 dated Jun. 3, 2009.
International Preliminary Report on Patentability for Application No. PCT/US2009/035070 dated Aug. 31, 2010.
International Preliminary Report on Patentability for Application No. PCT/US2010/025416 dated Sep. 9, 2011.
Office Action for Japanese Application No. 2011-552156 dated Feb. 3, 2014.
U.S. Appl. No. 12/528,571, filed Aug. 25, 2009; In re: deSimone; entitled *Discrete Size and Shape Specific Pharmaceutical Organic Nanoparticles*.
U.S. Appl. No. 12/918,916, filed Nov. 23, 2010; In re: Desimone et al., entitled *Delivery Apparatus and Associated Method*.
Belanger, Alain, "Therapeutic Electrophysical Agents: Evidence Behind Practice", 3rd Edition, Wolters-Kluwer (2015); Chapter 16: Iontophoresis.
Becker, Sid and Kuznetsov, Andrey, "Transport in Biological Media", Elsevier (2013). Chapter 11: Electrotransport Across Membranes in Biological Media: Electrokinetic Theories and Applications in Drug Delivery.
Westermeier, Reiner, "Electrophoresis in Practice", 4rd Edition, Wiley-VCH (2005).
Magdeldin, Sameh, "Gel Electrophoresis: Principles and Basics", IntechOpen (2012). Chapter 2: Gel-Electrophoresis and Its Applications.
M.B. Delgado-Charro, Iontophoretic drug delivery across the nail, Expert Opinion on Drug Delivery 9 (2012) 91-103.
Pillai, Omathanu et al., Transdermal iontophoresis. Part 1: Basic principles and considerations, University of Gerogia RAPID, Methods and findings in experimental and clinical pharmacology, (1999), 9 pages.
Chrambach, Andreas., Advanced Methods in the Biological Sciences, The Practive of Quantitative Gel Electrophoresis, (1985), 5 pages.
A.K. Banga, Electrically Assisted Transdermal and Topical Drug Delivery, Taylor and Francis, Bristol, PA, 1998.
S.K. Li, Transdermal delivery: technologies, in: J. Swarbrick (Ed.), Encyclopedia of Pharmaceutical Technology, Informa Healthcare, New York, 2007, pp. 3843-3853.
B.H. Sage, Iontophoresis, in: E.W. Smith, H.I. Maibach (Eds.), Percutaneous Penetration Enhancers, CRC Press, Boca Raton, 1995.
M.S. Roberts, P.M. Lai, S.E. Cross, N.H. Yoshida, Solute structure as a determinant of iontophoretic transport, in: R.O. Potts, R.H. Guy (Eds.), Mechanisms of Transdermal Drug Delivery, Marcel Dekker, New York, 1997.
E. Eljarrat-Binstock, A.J. Domb, Iontophoresis: a non-invasive ocular drug delivery, Journal of Controlled Release 110 (2006) 479-489.
Murthy, Narasimha et al., Iontophoretic Drug Delivery Across Human Nail, Department of Pharmaceutics, The University of Mississippi, (Jun. 26, 2006), 7 pages.
Ciccone, Charles., Clinical Electrophysiology Iontophoresis, Clinical Electrophysiology Electrotherapy and Electrophysiologic Testing, Second Edition, Ch. 9, (1989), 29 pages.

* cited by examiner

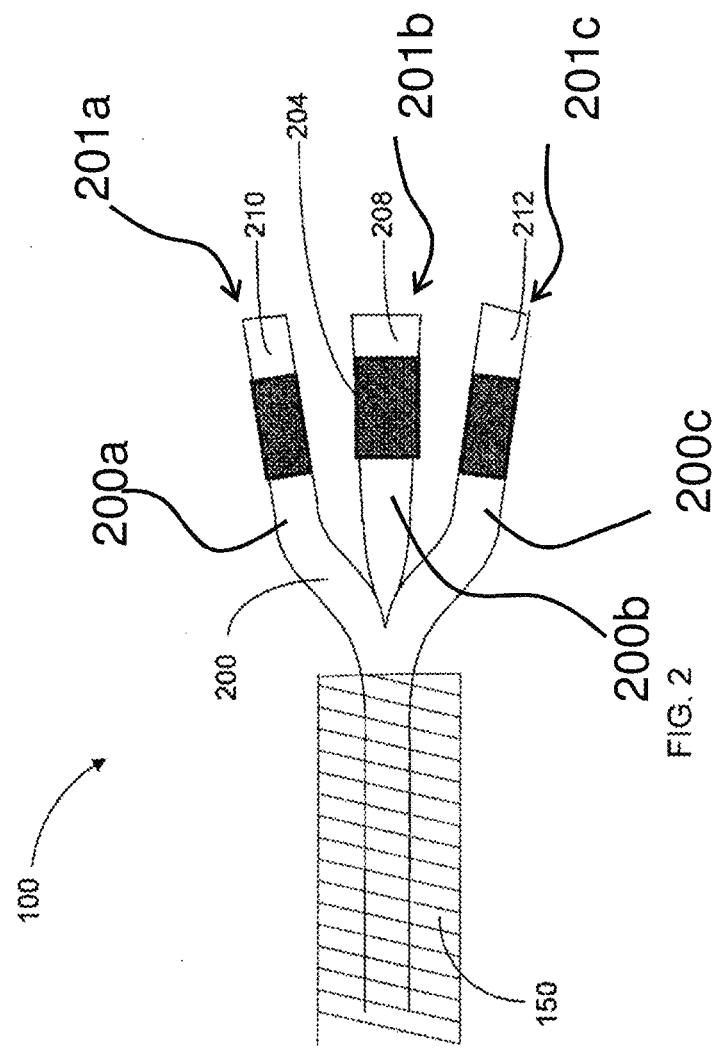

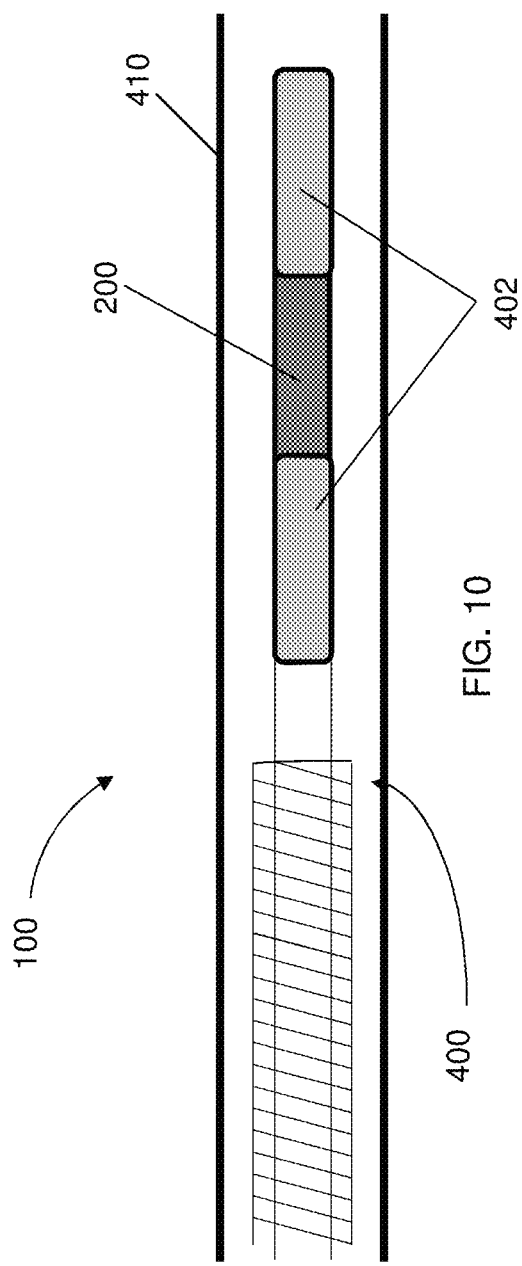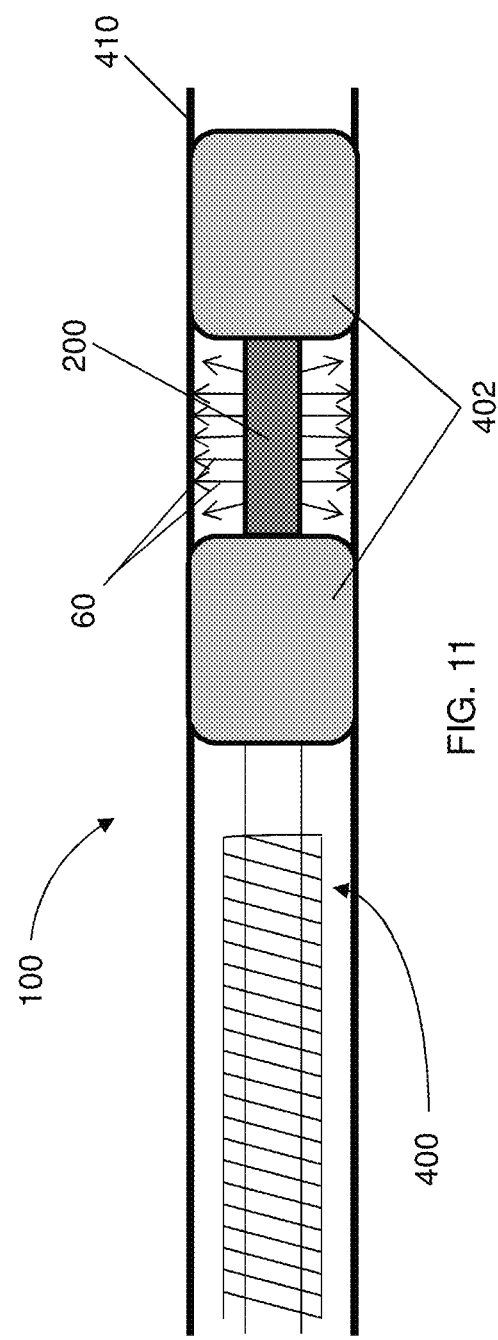

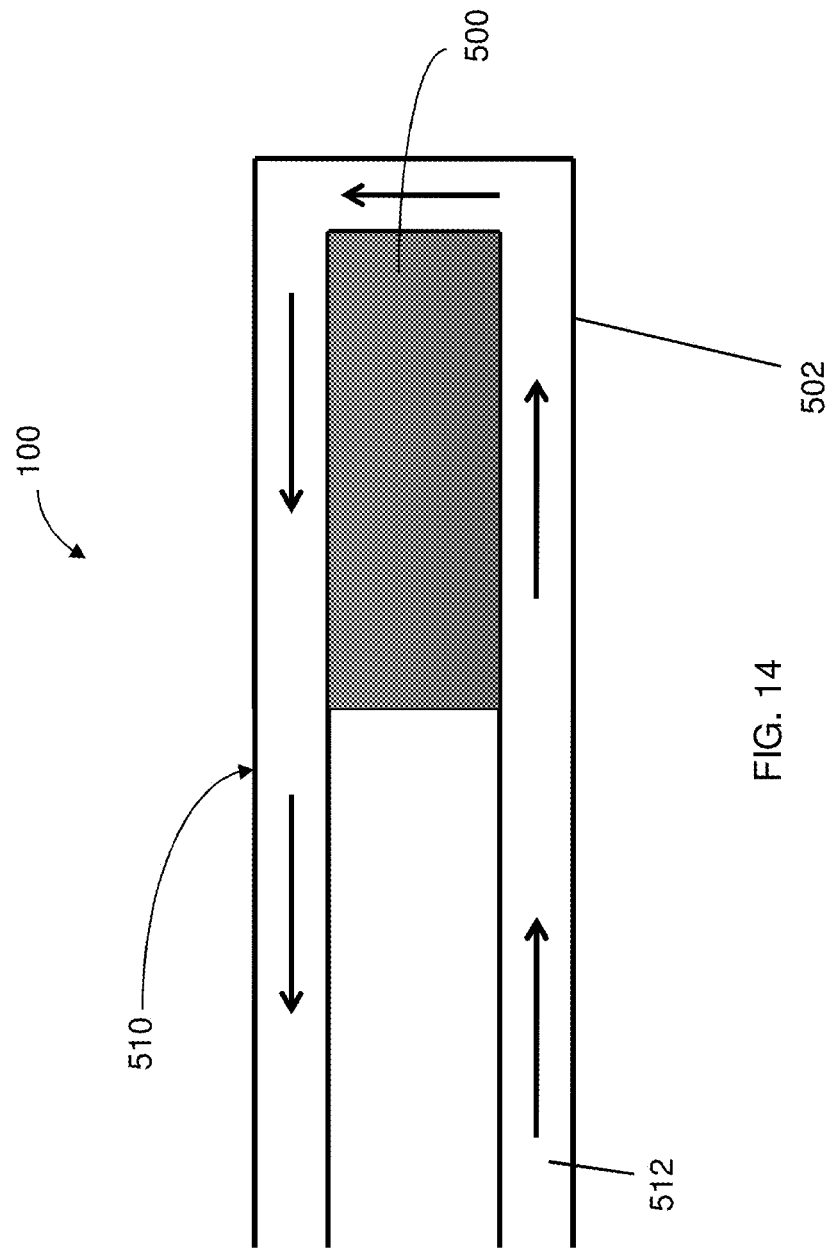

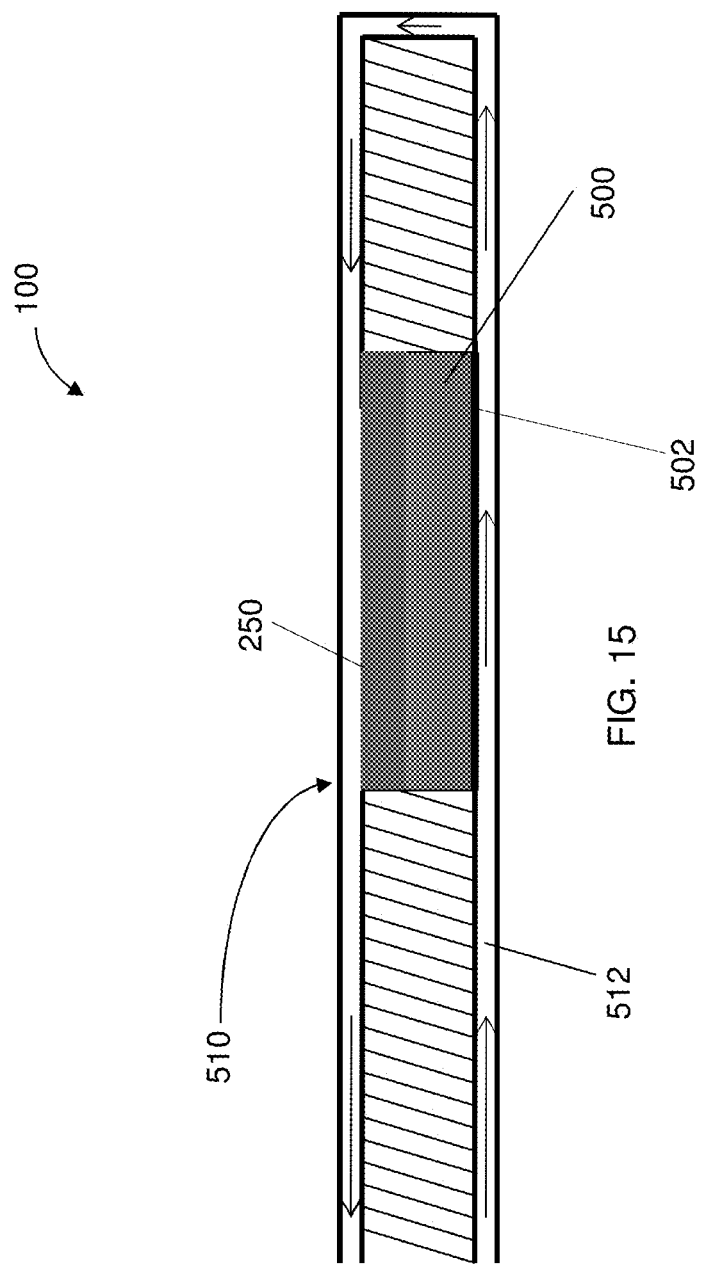

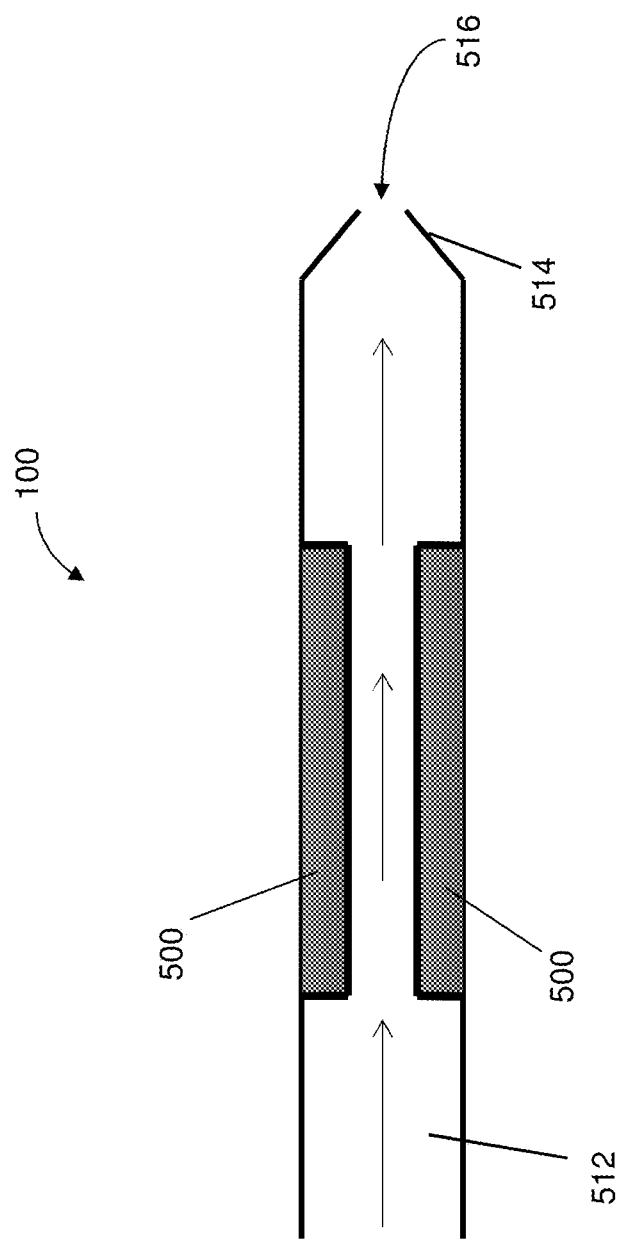

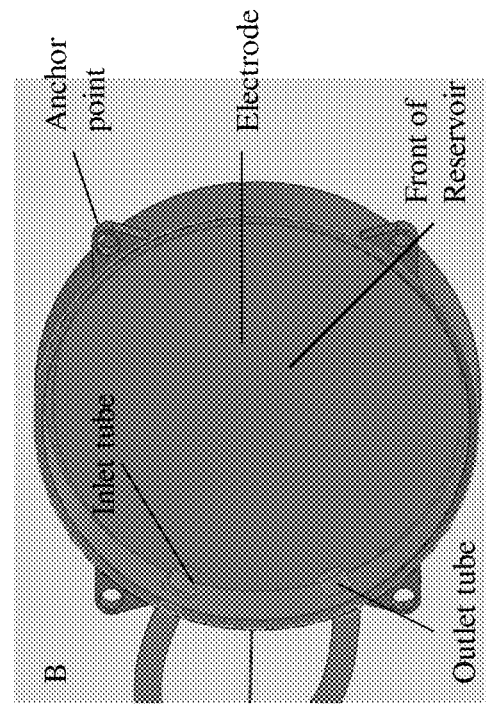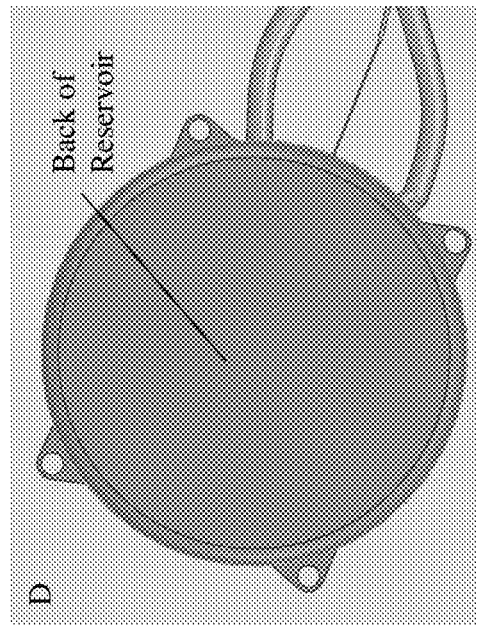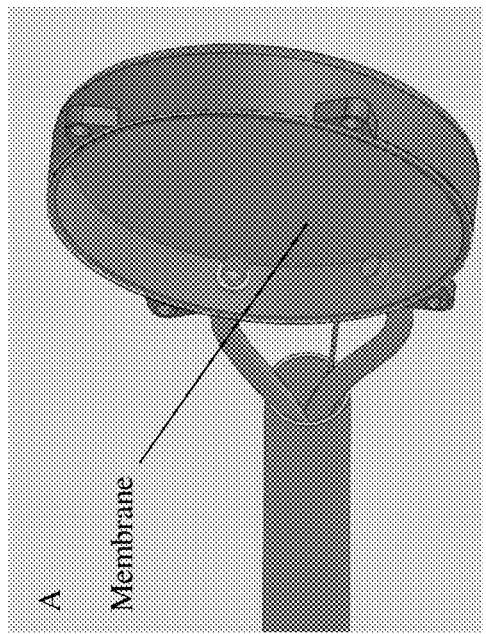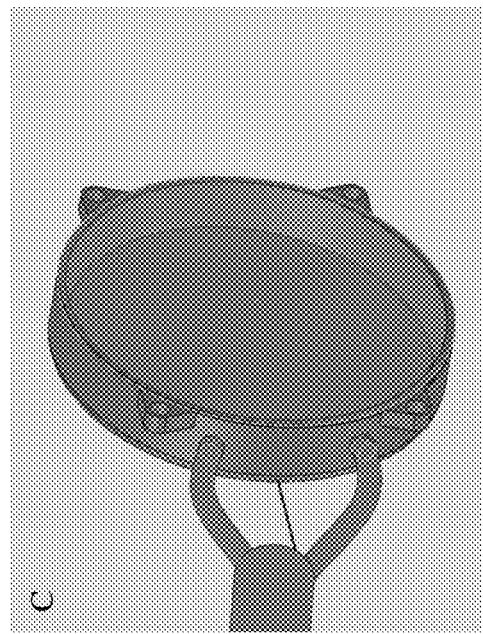
FIGS. 33A-D

INTERVENTIONAL DRUG DELIVERY SYSTEM AND ASSOCIATED METHODS

FEDERALLY SPONSORED RESEARCH OR DEVELOPMENT

This invention was made with government support under Grant Number CHE-9876674 awarded by the National Science Foundation. The government has certain rights in the invention.

BACKGROUND

Field of the Invention

Embodiments of the present invention relate to an interventional drug delivery system, and more particularly, to a system for facilitating delivery of various cargos, such as, for example, therapeutic agents, to target sites of internal body tissue in vivo, and methods associated therewith, wherein the system implements an electric field to drive cargo through tissue as in iontophoretic approaches.

Description of Related Art

Many techniques exist for the delivery of drugs and therapeutic agents to the body. Traditional delivery methods include, for example, oral administration, topical administration, intravenous administration, and intramuscular, intradermal, and subcutaneous injections. With the exception of topical administration which permits more localized delivery of therapeutic agents to particular area of the body, the aforementioned drug delivery methods generally result in systemic delivery of the therapeutic agent throughout the body. Accordingly, these delivery methods are not optimal for localized targeting of drugs and therapeutic agents to specific internal body tissues.

As a result, other methods, such as endovascular medical devices, Natural Orifice Translumenal Endoscopic Surgery (NOTES)-based devices, and iontophoresis, have been developed to provide localized targeting of therapeutic agents to a particular internal body tissue. Iontophoresis is a form of drug delivery that uses electrical current to enhance the movement of charged molecules across or through tissue. Iontophoresis is usually defined as a non-invasive method of propelling high concentrations of a charged substance, normally therapeutic or bioactive-agents, transdermally by repulsive electromotive force using a small electrical charge applied to an iontophoretic chamber containing a similarly charged active agent and its vehicle. In some instances, one or two chambers are filled with a solution containing an active ingredient and its solvent, termed the vehicle. The positively charged chamber (anode) repels a positively charged chemical, while the negatively charged chamber (cathode) repels a negatively charged chemical into the skin or other tissue. Unlike traditional transdermal administration methods that involve passive absorption of a therapeutic agent, iontophoresis relies on active transportation within an electric field. In the presence of an electric field, electromigration and electroosmosis are the dominant forces in mass transport. As an example, iontophoresis has been used to treat the dilated vessel in percutaneous transluminal coronary angioplasty (PTCA) and thus limit or prevent restenosis. In PTCA, catheters are inserted into the cardiovascular system under local anesthesia and an expandable balloon portion is then inflated to compress the atherosclerosis and dilate the lumen of the artery.

The delivery of drugs or therapeutic agents by iontophoresis avoids first-pass drug metabolism, a significant disadvantage associated with oral administration of therapeutic agents. When a drug is taken orally and absorbed from the digestive tract into the blood stream, the blood containing the drug first passes through the liver before entering the vasculature where it will be delivered to the tissue to be treated. A large portion of an orally ingested drug, however, may be metabolically inactivated before it has a chance to exert its pharmacological effect on the body. Furthermore it may be desirable to avoid systematic delivery all together in order to allow high doses locally while avoiding potential side effects elsewhere, wherein local delivery is desirable for localized conditions. Existing medical device technologies that enable localized placement of therapeutics fail to provide the opportunity to embed/secure therapeutics in the tissue(s) of interest.

Accordingly, it would be desirable to provide an improved system and method for selectively and locally targeting delivery of various drugs and therapeutic agents to an internal body tissue, and fixing such cargos in the tissue(s) of interest in vivo.

SUMMARY

The above and other needs are met by aspects of the present invention which provide, in one instance, a delivery system, and in particular, a delivery system for local drug delivery to a target site of internal body tissue. The delivery system comprises a source electrode adapted to be positioned proximate to a target site of internal body tissue. A counter electrode is in electrical communication with the source electrode. The counter electrode is configured to cooperate with the source electrode to form a localized electric field proximate to the target site. An electrode deployment device may be used and is configured to insert at least one of the source electrode and the counter electrode proximate to the target site of internal body tissue in vivo. A reservoir is capable of interacting with the localized electric field. The reservoir is configured to carry a cargo capable of being delivered to the target site when exposed to the localized electric field formed between the source electrode and the counter electrode. In some aspects, the drug reservoir is capable of being remotely filled with the cargo.

Another aspect provides a method for delivering a cargo to a target site of internal body tissue. Such a method comprises disposing a source electrode proximate to a target site of internal body tissue in vivo using an electrode deployment device, and disposing a counter electrode in electrical communication with the source electrode, wherein the counter electrode is configured to cooperate with the source electrode to form a localized electric field proximate to the target site. The method further comprises disposing a reservoir such that the reservoir is capable of interacting with the localized electric field. The reservoir is configured to carry a cargo capable of being delivered to the target site when exposed to the localized electric field formed between the source electrode and the counter electrode. In some aspects, the drug reservoir is capable of being remotely filled with the cargo. The method further comprises applying a voltage potential across the source and counter electrodes to form an electric field, thereby delivering at least a portion of the cargo to the target site.

Yet another aspect provides a method of treating a target site of internal body tissue. Such a method comprises delivering a therapeutic agent to a body cavity of a patient for storage thereof. The method further comprises positioning a first electrode proximate to a target site of body tissue, and positioning a second electrode such that the second electrode is in electrical communication with the first electrode. The method further comprises applying a voltage potential across the first and second electrodes to drive the therapeutic agent from the body cavity to the target site.

As such, embodiments of the present invention are provided to enable highly targeted and efficient delivery of various cargos to predetermined target sites. In this regard, aspects of the present invention provide significant advantages as otherwise detailed herein.

BRIEF DESCRIPTION OF THE DRAWINGS

In order to assist the understanding of embodiments of the invention, reference will now be made to the appended drawings, which are not necessarily drawn to scale. The drawing is exemplary only, and should not be construed as limiting the invention.

FIG. 2 is a partial view of a delivery system having a source electrode 200 with an array of probes 200a, 200b and 200c, according to an alternative embodiment of the present disclosure;

FIG. 10 is a partial view of a delivery system having a source electrode serially disposed between a pair of expandable members configured to occlude a target site, wherein the expandable members are in a relaxed state, according to one embodiment of the present disclosure;

FIG. 11 is a partial view of the delivery system of FIG. 10, illustrating the expandable members in an expanded state so as to occlude the target site such that delivery of a cargo is limited thereto;

FIG. 14 is a partial view of a delivery system having a coolant device extending about a counter electrode to provide cooling thereto, the coolant device having a membrane portion disposed about the counter electrode, according to one embodiment of the present disclosure;

FIG. 15 is a partial view of a delivery system having a coolant device extending about a counter electrode to provide cooling thereto, wherein the counter electrode is disposed between an insulating member and a membrane portion of the coolant device, according to one embodiment of the present disclosure;

FIG. 16 is a partial view of a delivery system having a coolant device extending about a counter electrode to provide cooling thereto, the coolant device having an aperture disposed at a distal end thereof for permitting a coolant substance to exit therefrom;

FIGS. 33A-33D depict various perspective views of a delivery system in accordance with another aspect of the present disclosure;

DETAILED DESCRIPTION OF THE PREFERRED EMBODIMENTS

Figure 1A:
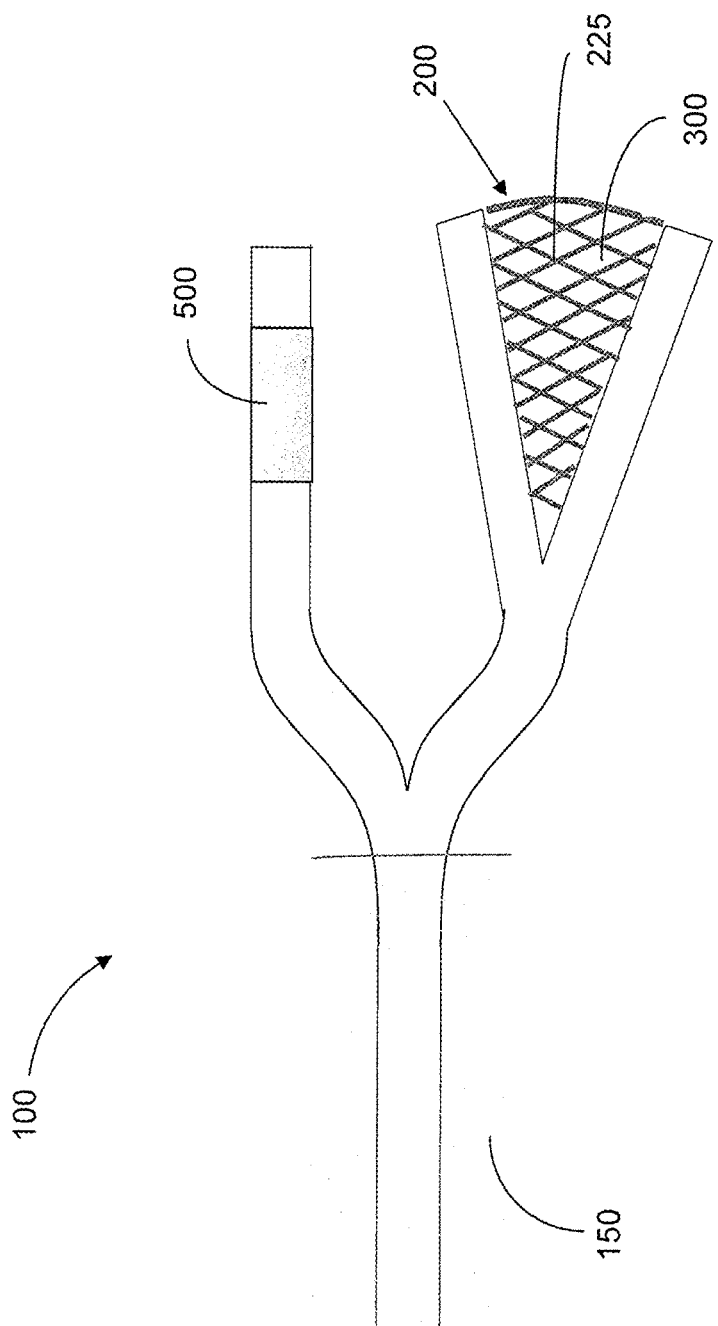
FIGS. 1A-1G are schematic drawings of various embodiments of a delivery system having a source electrode and counter electrode configured to cooperate to form an electric field for delivering a cargo, according to one embodiment of the present disclosure.
Figure 1B:
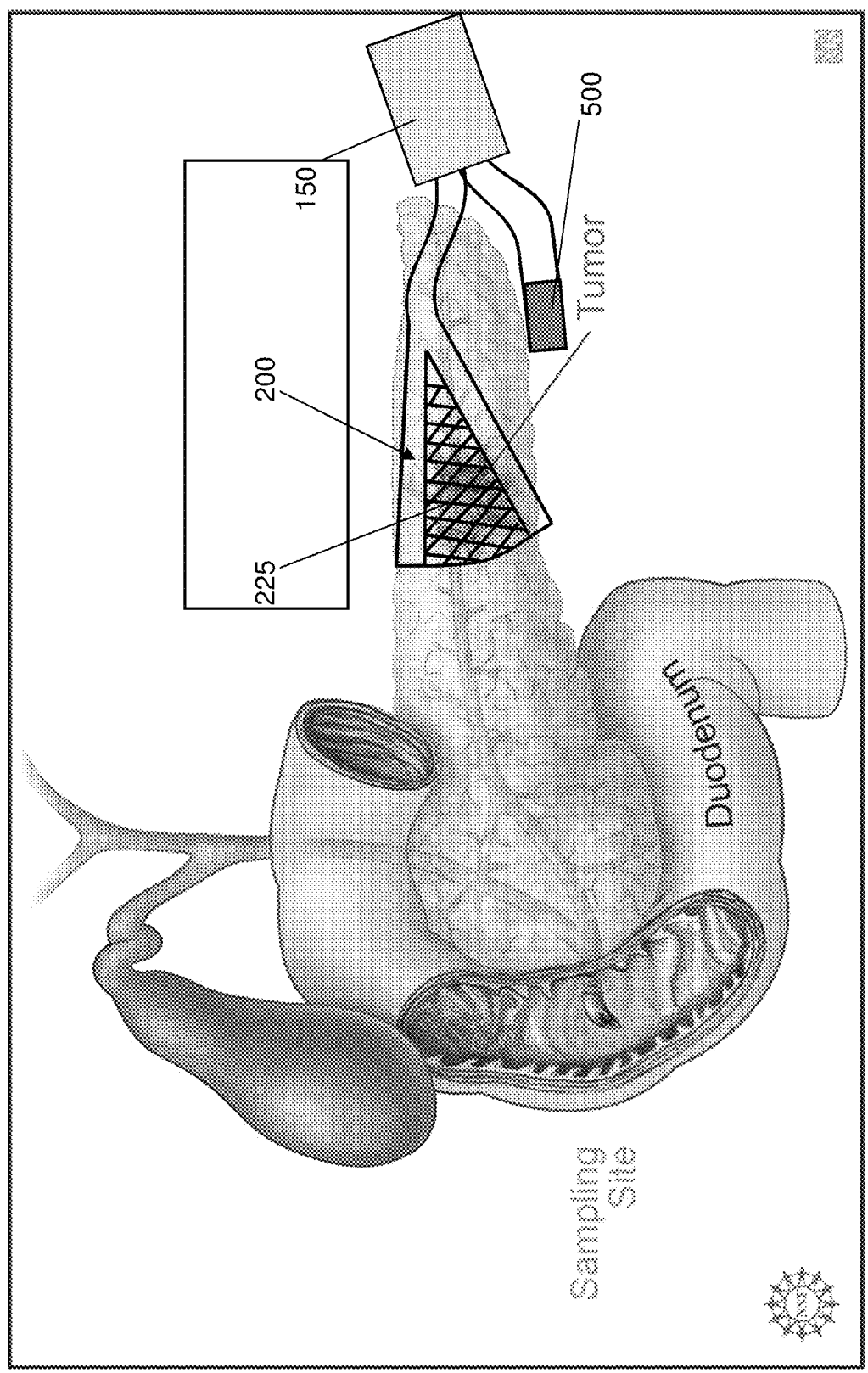

Embodiments of the present invention now will be described more fully hereinafter with reference to the accompanying drawings. The invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention are directed to systems and methods for delivering treatment or therapeutic agents (otherwise referred to herein as "cargo") to specific locations, including intracellular locations in a safe and effective manner. Such systems may deliver the agents to a diseased site in effective amounts without endangering normal tissues or cells and thus reduce or prevent the occurrence of undesirable side effects. Further, such systems may electrically enhance the local delivery of treatment agents into the wall tissues or cells of the living body. These systems are designed to target certain tissue and cell locations and deliver the treatment agents directly to those locations, while minimizing any effects on non-targeted tissues and cells. In particular, embodiments of the present invention relate to systems which provide an electrical driving force that can increase the rate of migration of drugs and other therapeutic agents out of a reservoir into body tissues and cells using iontophoresis and other approaches.

More particularly, embodiments of the present invention rely on the transport of charged and uncharged species under the influence of a localized electric field generated at the site of interest. The overall transport of charged and uncharged species is based upon three characteristic driving forces, which includes passive diffusion, electroosmosis, and electromigration. Passive diffusion involves the movement of a chemical species from a region of high concentration to an area of low concentration. Electroosmosis is the movement of a solute species via a solvent flow accompanied by the movement of an extraneous charged species. Electroosmosis encompasses the solvent flow referred to as hydrokinesis. Electromigration is the movement of a charged species through an applied electric field to an electrode of opposite polarity. Transport of a neutrally charged species is driven by passive diffusion and electroosmosis only, whereas all transport modalities, passive diffusion, electroosmosis, and electromigration contribute to the flux of a charged species.

In this regard, embodiments of the present invention may provide an interventional drug delivery system and methods for localized delivery of therapeutic agents to internal locations in the human body using a controlled electrical field. The systems may be constructed to deliver the agents specifically to the site of interest, improving penetration of the agent while limiting effect upon non-targeted tissue. Embodiments of the present invention may be fashioned to deliver the agents via intravascular, intraperitoneal, minimally invasive surgery, and natural orifice transluminal endoscopic surgery (NOTES) modalities. The action of the electric field may be controlled through a programmable power supply or a function generator. By using various electrode designs and placement configurations, highly localized and focused delivery of cargo to the tissue of interest may be achieved. The overall controlled release characteristics of the delivery system may be dependent upon the charge, size, conductivity, concentration, and $pK_a$ of the chemical species and nanoparticles, pH of the surrounding environment, resistance of the site of interest, current and voltage applied, electrode design and amount of extraneous ions at site of interest.

Embodiments of the present invention may be implemented in the delivery of therapeutic agents for such diverse areas as oncology, pulmonary, gastrointestinal (GI), and neurology applications. Embodiments of the present invention find application in the field of interventional oncology for the treatment of various cancers, which may include, for example, pancreatic cancers, lung cancer, esophageal cancers, bladder cancers, colorectal cancers, liver cancers, hepatic metastases, bile duct cancers, renal cancers, cervical cancers, prostate cancers, ovarian cancer, thyroid cancers, uterine cancers, and leukemia. In particular, accessing bone marrow tissue may be advantageous. Other applications may cover pulmonary diseases, neurological disorders as well as cardiovascular applications.

In some instances, embodiments of the present invention may employ an approach using iontophoresis. As used herein, the term "iontophoresis" means the migration of ionizable molecules through a medium driven by an applied low level electrical potential. This electrically mediated movement of molecules into tissues is superimposed upon concentration gradient dependent diffusion processes. If the medium or tissue through which the molecules travel also carries a charge, some electro-osmotic flow occurs. However, generally, the rate of migration of molecules with a net negative charge towards the positive electrode and vice versa is determined by the net charge on the moving molecules and the applied electrical potential. The driving force may also be considered as electrostatic repulsion. Iontophoresis usually requires relatively low constant DC current in the range of from about 2-5 mA. The applied potential for iontophoresis will depend upon number of factors, such as the electrode configuration and position on the tissue and the nature and charge characteristics of the molecules to be delivered.

The present invention relates to the delivery of cargo including, but not limited to, therapeutic agents such as drug molecules, proteins, peptides, antibodies, antibody scaffolds or fragments of antibodies, nucleotides, contrast agents and dyes (including radiolabels, fluorophores and chelated magnetic species), liposomes, micelles, nanoparticles, multimolecular aggregates (such as, for example, albumin/paclitaxel or Abraxane™) and combinations thereof, with or without cargo and/or targeting capabilities. Small molecules may include chemotherapeutic agents such as alkylating agents, antimetabolites, plant alkaloids and terpenoids, vinca alkaloids, podophyllotoxin, taxanes, topoisomerase inhibitors, and antitumor antibiotics, as well as analgesics and local anesthetics. Embodiments of the present invention also covers the delivery of pro-drugs, small molecules and nanoparticles, in some instances having neutral charge before delivery, that may be subsequently charged or triggered to release cargo under physiological conditions.

Furthermore, the cargo may include small ionic molecules, nucleic acids, proteins, therapeutic agents, diagnostic agents, and imaging agents as well as organic nanoparticles which may encapsulate a wide range of therapeutic, diagnostic, and imaging agents. The cargo may be configured to traffic preferentially based on size, shape, charge and surface functionality; and/or controllably release a therapeutic. Such cargos may include but are not limited to small molecule pharmaceuticals, therapeutic and diagnostic proteins, antibodies, DNA and RNA sequences, imaging agents, and other active pharmaceutical ingredients. Further, such cargo may include active agents which may include, without limitation, analgesics, anti-inflammatory agents (including NSAIDs), anticancer agents, antimetabolites, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, therapeutic proteins, enzymes, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, and antiviral agents. In addition, the cargo may include a polynucleotide. The polynucleotide may be provided as an antisense agent or interfering RNA molecule such as an RNAi or siRNA molecule to disrupt or inhibit expression of an encoded protein.

Other cargo may include, without limitation, MR imaging agents, contrast agents, gadolinium chelates, gadolinium-based contrast agents, radiosensitizers, such as, for example, 1,2,4-benzotriazin-3-amine 1,4-dioxide (SR 4889) and 1,2,4-benzotriazine-7-amine 1,4-dioxide (WIN 59075); platinum coordination complexes such as cisplatin and carboplatin; anthracenediones, such as mitoxantrone; substituted ureas, such as hydroxyurea; and adrenocortical suppressants, such as mitotane and aminoglutethimide.

In other embodiments, the cargo may comprise Particle Replication In Non-wetting Templates (PRINT) nanoparticles (sometimes referred to as devices) such as disclosed, for example, in PCT WO 2005/101466 to DeSimone et al.; PCT WO 2007/024323 to DeSimone et al.; WO 2007/030698 to DeSimone et al.; and WO 2007/094829 to DeSimone et al., each of which is incorporated herein by reference. PRINT is a technology which produces monodisperse, shape specific particles which can encapsulate a wide variety of cargos including small molecules, biologics, nucleic acids, proteins, imaging agents. Cationically charged PRINT nanoparticles smaller than 1 micron are readily taken up by cells over a relatively short time frame, but penetration of the particles throughout the tissue is a longer process. For the delivery of PRINT nanoparticles throughout the tissue to be effective, the penetration needs to occur within a reasonable operational time frame. As such, the delivery system may be used to achieve such penetration by employing iontophoresis, in which charged PRINT nanoparticles are driven into body tissue using repulsive electromotive forces. The PRINT particles may or may not contain a therapeutic. In some instances, the particle may be comprised of PLGA. In addition, the PRINT nanoparticles may be engineered to achieve a certain mission, and design-in handles that permit remote control for externally turning the cargo "on" or switching it "off". As such, the cargo may be manipulated using ultrasound, low-dose radiation, magnetics, light and other suitable mechanisms. The particles may be coated with gold such as, for example, gold nano-shells for thermal ablation therapy.

FIGS. 1-15 illustrate various embodiments and aspects of a delivery system 100 in accordance with the present invention. In general, the delivery system is provided for delivering a cargo to, or through, a localized area of a passageway or other internal body tissue in order to treat the localized area of the passageway or tissue with minimal, if any, undesirable effect on other body tissue. Such a system may be implemented intraluminally, through natural orifices, or by minimally invasive surgery such that the system may be used in vivo. The delivery system 100 may generally include a source electrode, a counter electrode, a reservoir for carrying a cargo (e.g., a therapeutic agent), and an electrode deployment device.

As described previously, the delivery apparatus 100 which may deliver cargo iontophoretically to target sites for localized treatment. In general, iontophoresis technology uses an electrical potential or current across a target site (e.g., a semipermeable barrier) to drive ionic fixatives or drugs (or drive nonionic fixatives or drugs) in an ionic solution. Iontophoresis facilitates both transport of the fixative or drug across the target site and enhances tissue penetration. In the application of iontophoresis, two electrodes, a source electrode and a counter electrode (in some instances, the electrodes may be positioned on opposing sides of the target site, though such a configuration or arrangement is not required), are utilized to develop the required potential or current flow. The positioning of the electrodes may be accomplished using an electrode deployment device 150. The electrode deployment device 150 may be capable of positioning the source electrode, the counter electrode, and the reservoir such that the therapeutic agents may be delivered through intravascular, intraperitoneal, and natural orifice transluminal endoscopic surgery (NOTES) modalities. Some embodiments of the present invention may employ the technique of reverse iontophoresis, wherein a small molecule or other substance may be extracted from the surrounding medium. In this manner, toxic substances or excess cargo materials may be removed from locations in vivo.

In some instances, the electrode deployment device 150 may comprise a catheter device to be deployed in vivo using the intravascular route. In other embodiments, the electrode deployment device 150 may comprise an endoscopic device for deployment via natural orifices in the body. In other instances, the electrode deployment device 150 may comprise a laparoscopic device for minimally invasive surgical intervention. In other embodiments, the electrode deployment device 150 may be surgically implanted in a suitable location in vivo, such as, for example, the peritoneal cavity. In yet other instances, the electrode deployment device 150 may implement combinations of two or more of the embodiments listed above. According to some embodiments, the electrode deployment device 150 may locate the source electrode, counter electrode, and/or reservoir at the target site of interest through use of an imaging system.

FIGS. 1-11 illustrate various embodiments of a source electrode 200 implemented by the delivery system 100. The repulsive force for driving the charged cargo through the target site tissue is generated by placing the source electrode 200 at or proximate to the target site of interest. The delivery system 100 may include one or more source electrodes 200. By optimizing the placement and geometric profile of the source electrode(s) 200, considerable control may be achieved over the penetration depth, direction and overall area of delivery of the cargo to the target site. The source electrode(s) 200 may be configured as a single probe or an array of probes comprised, for example, of thin wires, foil, mesh, pellets, disks, stents, clamps, prongs, clips, needles, hollow tubes or combinations thereof. For example, as shown in FIG. 1, the source electrode 200 may include a mesh arrangement 225 (see also FIGS. 1B, 1C, and 18B) opposably positioned with respect to a counter electrode 500. In accordance with such an embodiment, in some instances, the counter electrode 500 may be positioned, for example, on an exterior surface of the pancreas/organ of interest. The source electrode 200 having the mesh arrangement 225 may also be placed on the exterior surface to cover a specific target tissue such as, for example, a tumor, as shown in FIG. 1B.

Figure 1C:
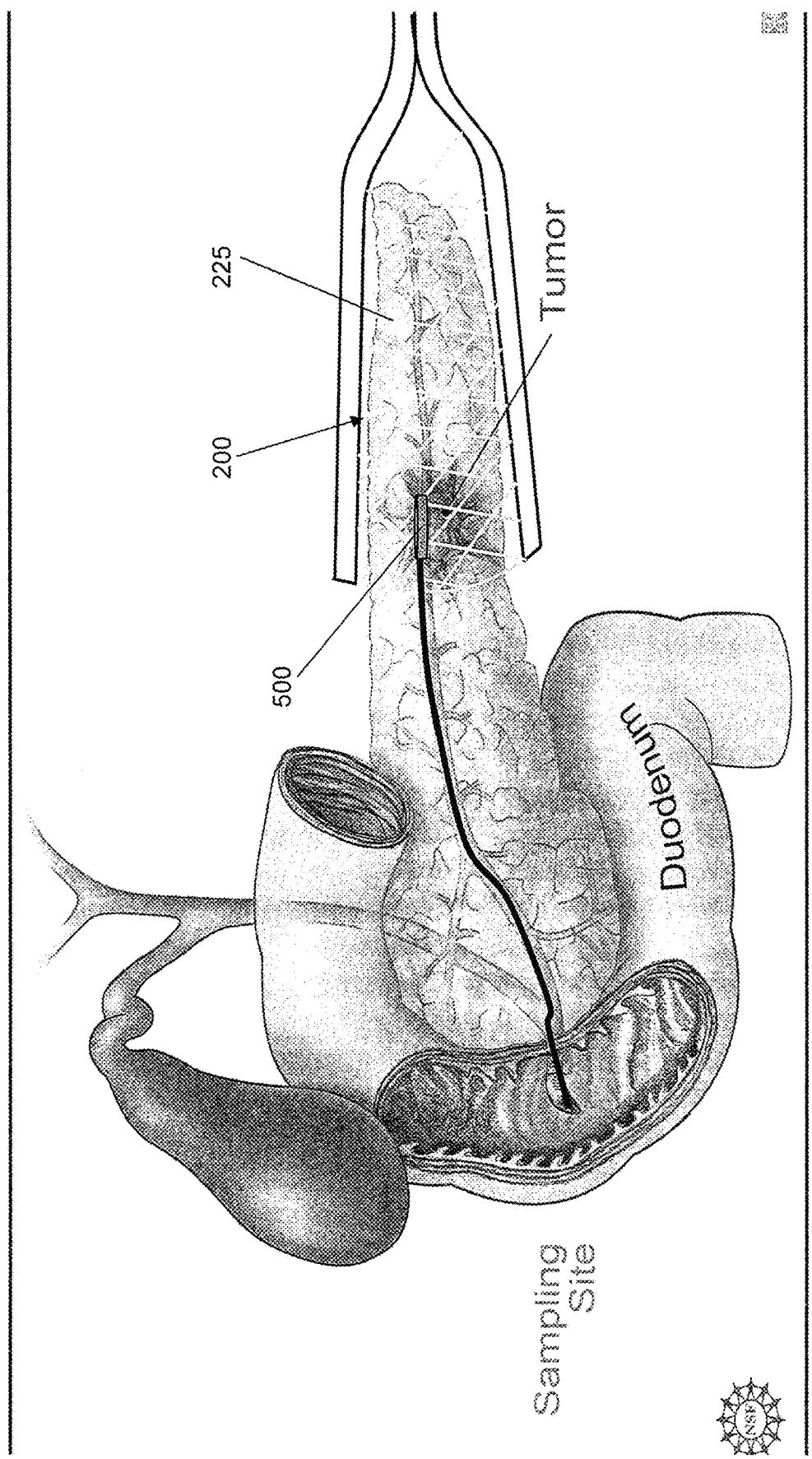
Figure 1D:
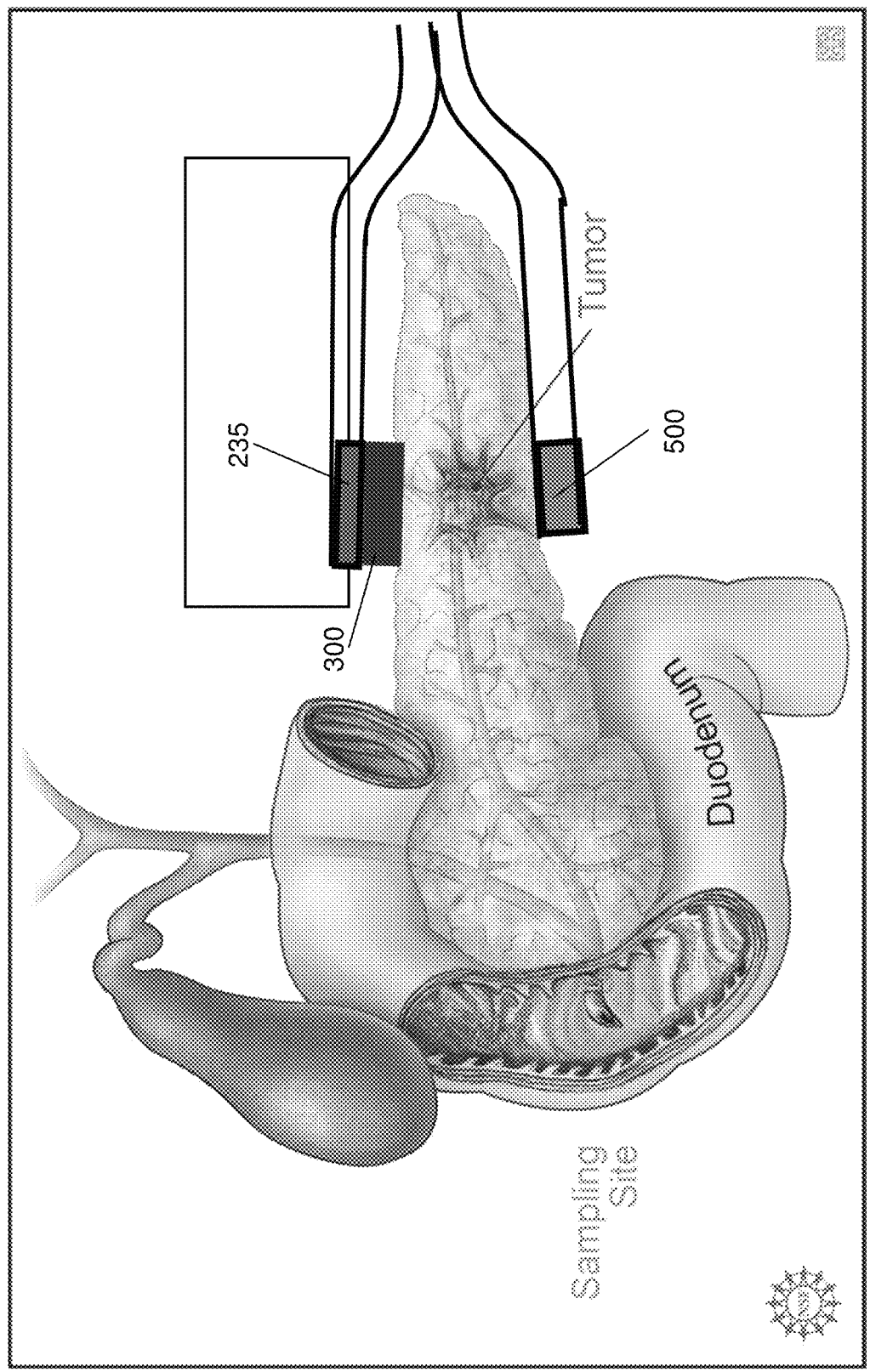
Figure 1E:
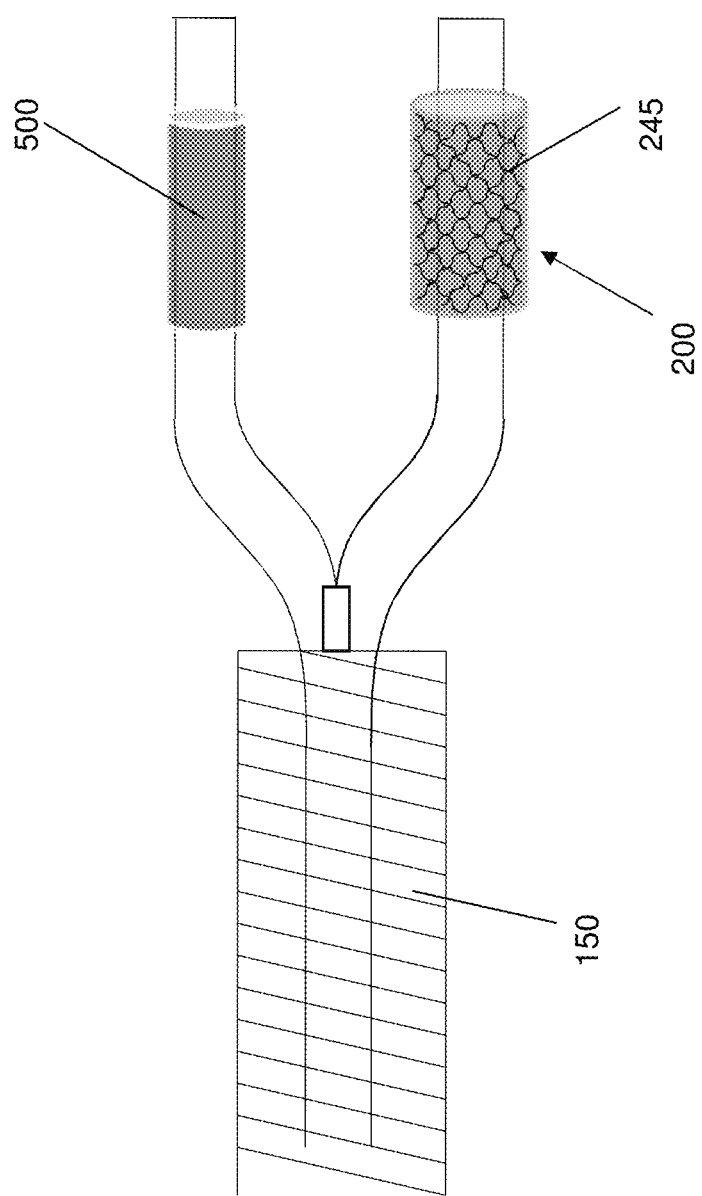
Figure 1F:
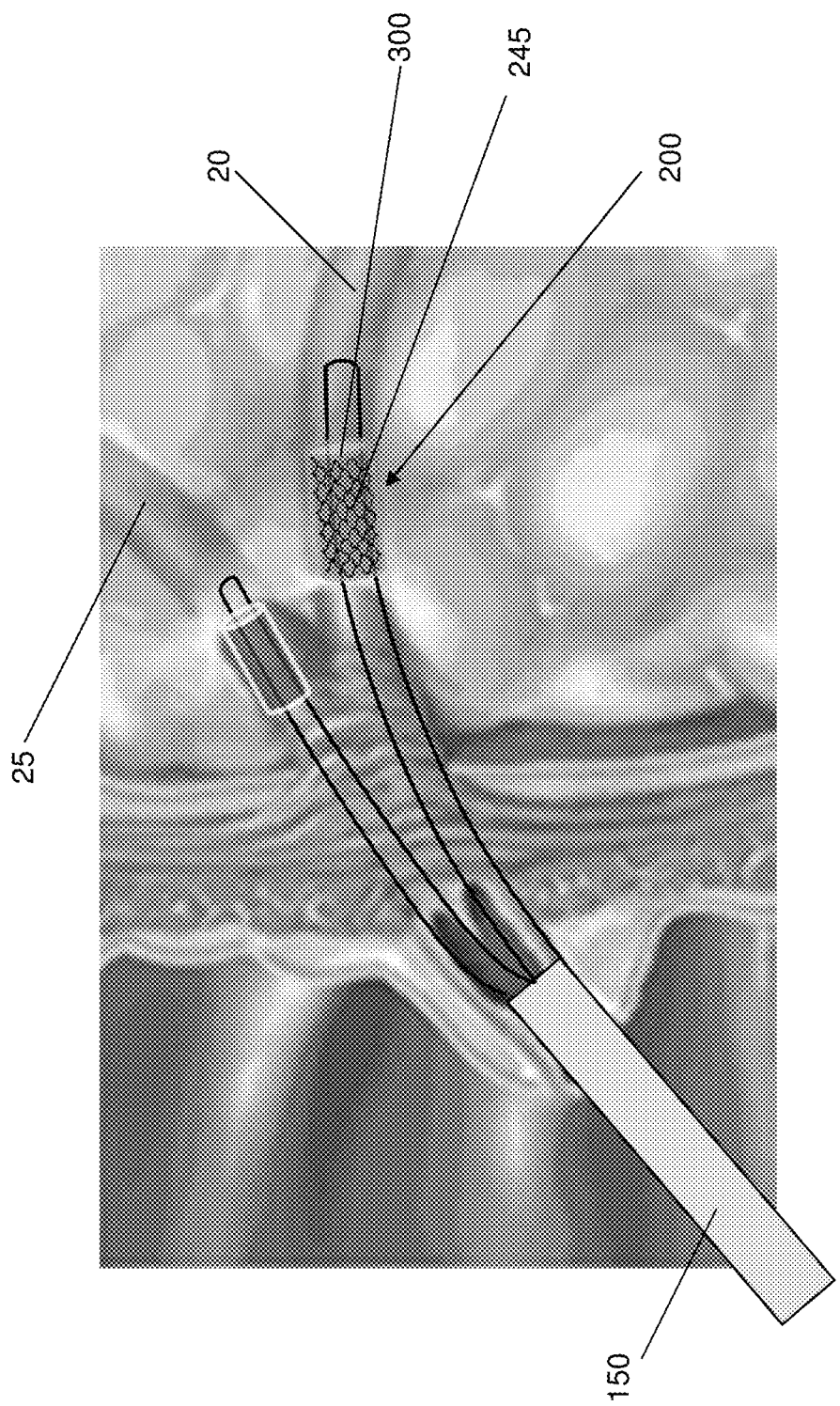
Figure 1G:
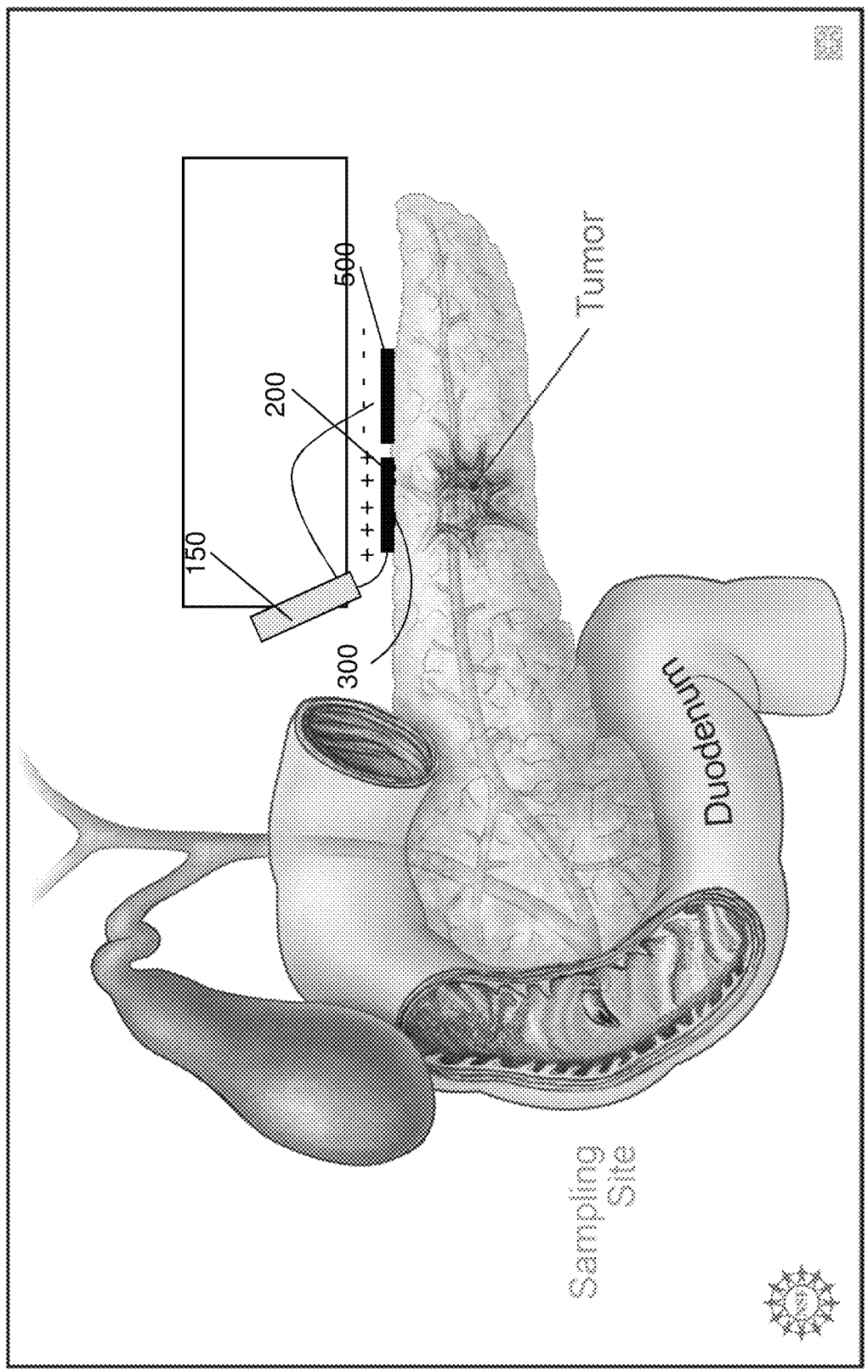

In another embodiment, the mesh arrangement 225 source electrode 200 may be configured to encase part or a portion of the target tissue (e.g., a conical mesh encasing the tail of the pancreas, as shown in FIG. 1C). In other instances, the source electrode 200 may be configured or arranged as foil or patch electrodes 235, as shown in FIG. 1D, wherein the drug reservoir 300 is coupled to the source electrode 200. The patch source electrode 235 may be configured as clamps or prongs situated at the end of the electrode deployment device 150, such as, for example, an endoscopic or laproscopic device, as shown in FIG. 2, wherein an intermediary prong 208 may include the patch source electrode 235. In this regard, the configuration may be modified to be internally deployed by the electrode deployment device 150, wherein the mesh arrangement 225 may be replaced by a stent device 245 (acting as the source electrode 200), as shown in FIG. 1E, that is positioned within the pancreatic duct 20, while the counter electrode 500 may be positioned within an alternate branch of the same duct or, alternatively, the bile duct 25 for example, as shown in FIG. 1F. In some instances, the source electrode may include a reservoir 300 coupled or otherwise attached thereto for holding the cargo to be delivered to the target site. In this manner, the reservoir 300 and/or the tissue of interest may be at least partially disposed between the source electrode 200 and the counter electrode 500. The source electrode(s) 200 may be fabricated from various materials including, but not restricted to, conducting metals, such as silver, silver chloride, platinum, aluminum, or conducting polymers such as polypyrrole, polyaniline, or polyacetylene. In some instances, both the source electrode 200 and the counter electrode 500 may be patch source electrodes 235, which may be positioned in a side-by-side or otherwise proximally positioned on an organ, tissue, or other target site, as shown in FIG. 1G. That is, the cargo of the reservoir 300 may penetrate the target site to reach, for example, a tumor when the voltage potential is applied between the source electrode 200 and the counter electrode 500. Of course, the patch source electrodes 235 may be on opposite sides of the organ, tissue, or target site, or may be otherwise appropriately configured to deliver the cargo to the target site.

Figure 3:
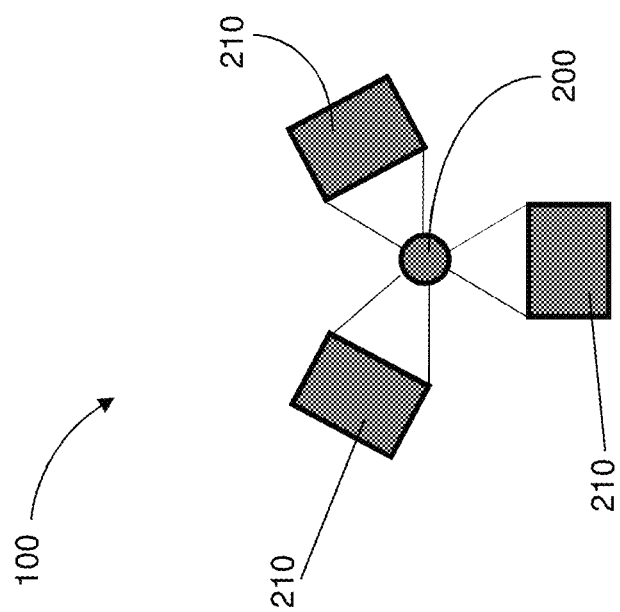
FIG. 3 is a partial view of a delivery system having a source electrode with an array of probes, according to yet another embodiment of the present disclosure.

According to some embodiments, the source electrode 200 may include an array of multi-functional probes, combining imaging and drug delivery functionalities, as illustrated in FIGS. 2 and 3 and indicated by reference numbers 200*a*, 200*b* and 200*c*. In this regard, the use of paramagnetic or radio-opaque materials in the probe body may be used for imaging purposes. In other instances, catheter devices may be capable of simultaneous delivery of imaging agents. According to other embodiments, the incorporation of a light source and camera may be incorporated into the probe for endoscopic devices. Various combinations of such imaging and delivery probes may be implemented by the delivery system 100. For example, as illustrated in FIG. 2, the intermediary prong 208 may include the electrode element 204, while the outer prongs 210, 212 include imaging devices and/or agents capable of assisting with positioning of the source electrode 200. With reference to FIG. 3, the electrode element 204 may be radially surrounded by imaging devices 210 or agents, other source electrodes 200 or other probe members, which may be configured as dependent on the location of the target site within a patient's body.

Figure 4:
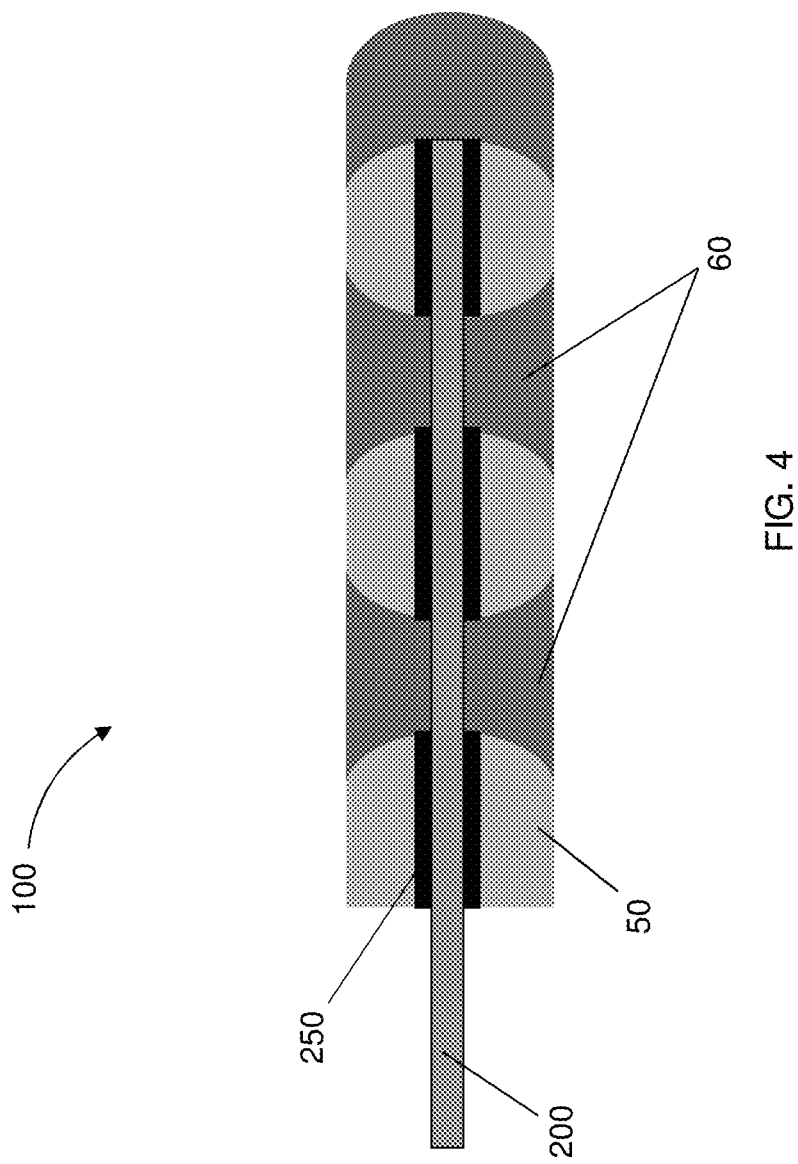
FIG. 4 is a partial view of a delivery system according to one embodiment of the present disclosure, illustrating a source electrode having a plurality of insulating members engaged therewith.

In some instances, the source electrode 200 may have one or more insulating layers or members 250*a*, 250*b*, 250*c* and 250*d* attached, connected, or otherwise engaged therewith. The insulating members 250*a*, 250*b*, 250*c* and 250*d* are provided to confer directionality to the transport profile of the cargo 60 with respect to the target site, as shown in FIG. 4, illustrating the source electrode 200 disposed within a tissue lumen 50. That is, the flux of the cargo will be attenuated corresponding to the insulated areas of the source electrode 200. In this regard, a partially insulated source electrode 200 may be for control over targeted delivery to specific in vivo locations. That is, by insulating a portion of the source electrode surface, control over delivery to the tissue or organ systems may be accomplished in a well defined manner. In this regard, the extent of transport from the sections of the target site exposed to the unshielded sections of the source electrode 200 may be greater than that of the transport from the shielded or insulated region of the source electrode 200.

Figure 5:
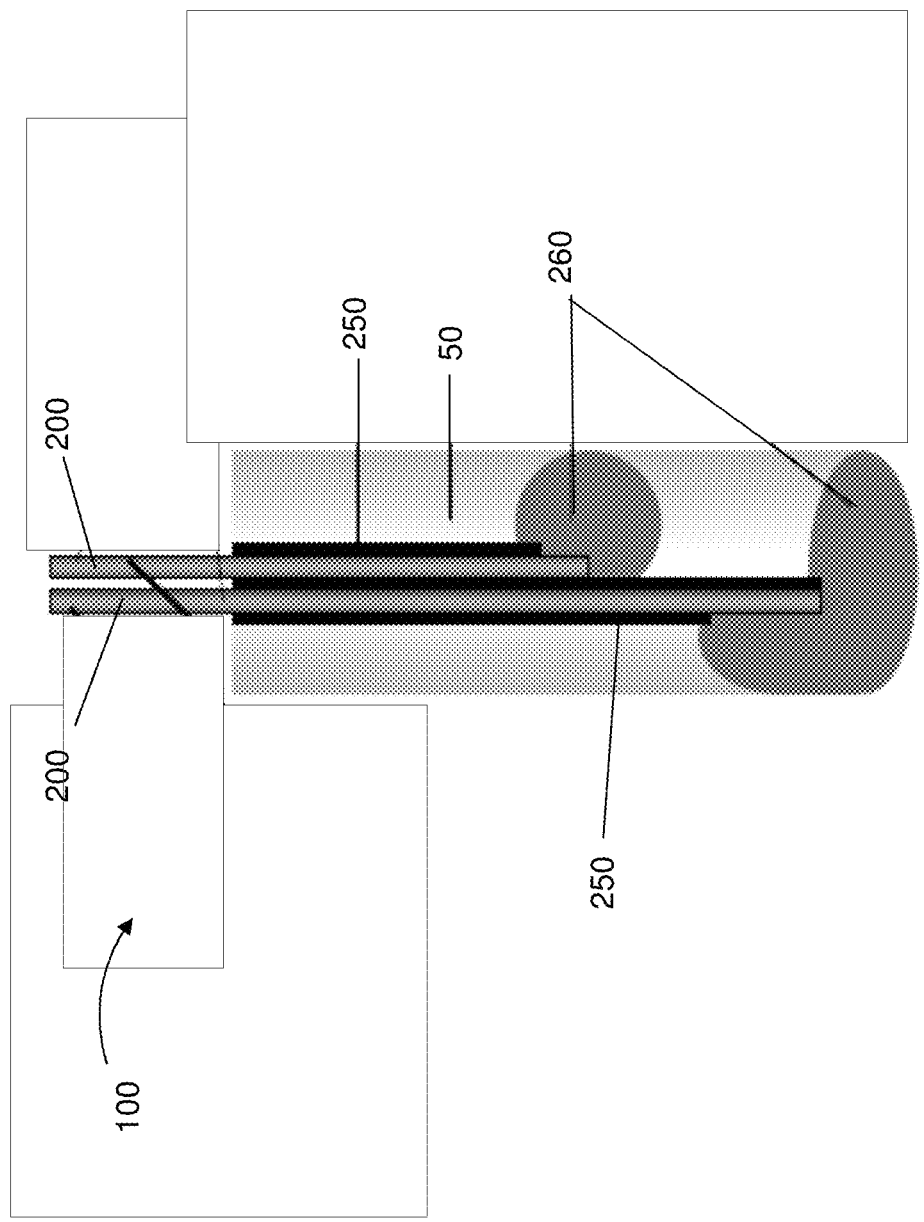
FIG. 5 is a partial view of a delivery system disposed within a tissue lumen, the delivery system having a plurality of independently controlled source electrodes and a plurality of insulating members configured to provide controlled delivery zones for specific targeting of target sites of the tissue lumen, according to one embodiment of the present disclosure.
Figure 6:
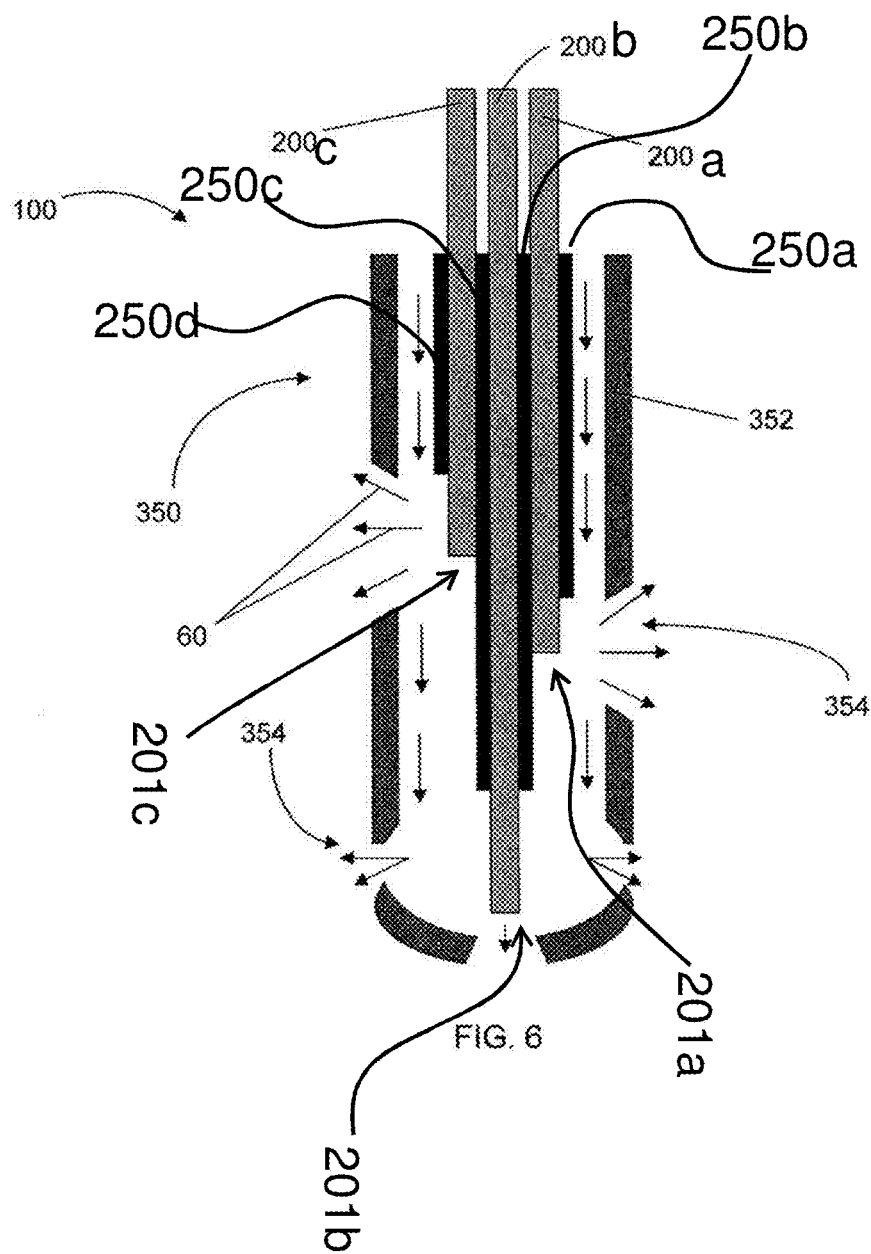
FIG. 6 is a partial view of a delivery system employing a catheter device for positioning of a source electrode 200, wherein the delivery system includes a plurality of independently controlled source electrodes 200a, 200b and 200c and a plurality of insulating members 250a, 250b, 250c and 250d configured to provide controlled delivery zones for specific targeting of target sites, according to one embodiment of the present disclosure.

According to some aspects of the present invention, a plurality of source electrodes and indicated by reference numbers 200*a*, 200*b* and 200*c* may be provided, wherein each source electrode 200*a*, 200*b* or 200*c* is independently controlled with respect to the other source electrodes 200*a*, 200*b* and 200*c*. In this manner, the delivery system 100 may be manipulated to target various sites for delivery of the cargo 60, as shown in FIG. 5, illustrating the source electrodes 200a, 200b and 200c disposed within a tissue lumen 50. That is, by allowing independent control over parameters for iontophoretic delivery such as current, voltage and time, variable delivery zones may be created at distinct sites within the same tissue lumen. In addition, the source electrodes 200 may terminate at various lengths to further provide control over deliver of the cargo to the target site(s). Furthermore, in some instances, the plurality of source electrodes 200a, 200b and 200c may have the insulating members 250a, 250b, 250c and 250d disposed therebetween and thereabout to also specifically designate delivery regions 260 for delivery of the cargo 60 to the target site(s). According to an alternative embodiment, the source electrodes may be disposed within the electrode deployment device 150, such as, for example, a catheter device 350, as illustrated in FIG. 6. The catheter device 350 may be comprised of a perforated polymer sheath 352. That is, the catheter device 350 may have a plurality of perforations 354 defined thereby such that the cargo 60 may exit the catheter device 350. In one particular embodiment, the source electrodes 200a, 200b and 200c terminate at different lengths and may be independently powered such that the probes are capable of being variably controlled. The source electrodes 200a, 200b and 200c may include the insulating members 250 disposed about and between the source electrodes 200a, 200b and 200c so as to form cargo delivery zones substantially aligned with the perforations 354 of the catheter device 350. In this regard, the cargo 60 may be fed through the catheter device 350 proximate to the target site at the terminal portion of the catheter device 350, where the cargo 60 may be drawn therefrom due to the electrical field applied across the source electrode 200a, 200b and 200c and the counter electrode.

Figure 7:
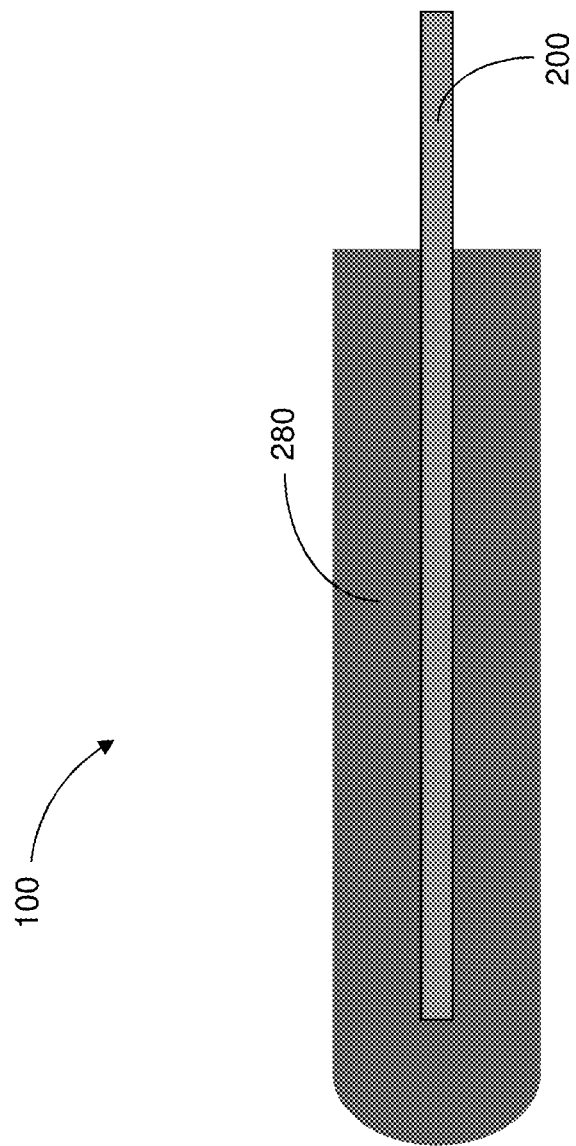
FIG. 7 is a partial view of a delivery system having a source electrode encapsulated by a polymer matrix reservoir having a cargo contained therein, according to one embodiment of the present disclosure.
Figure 8:
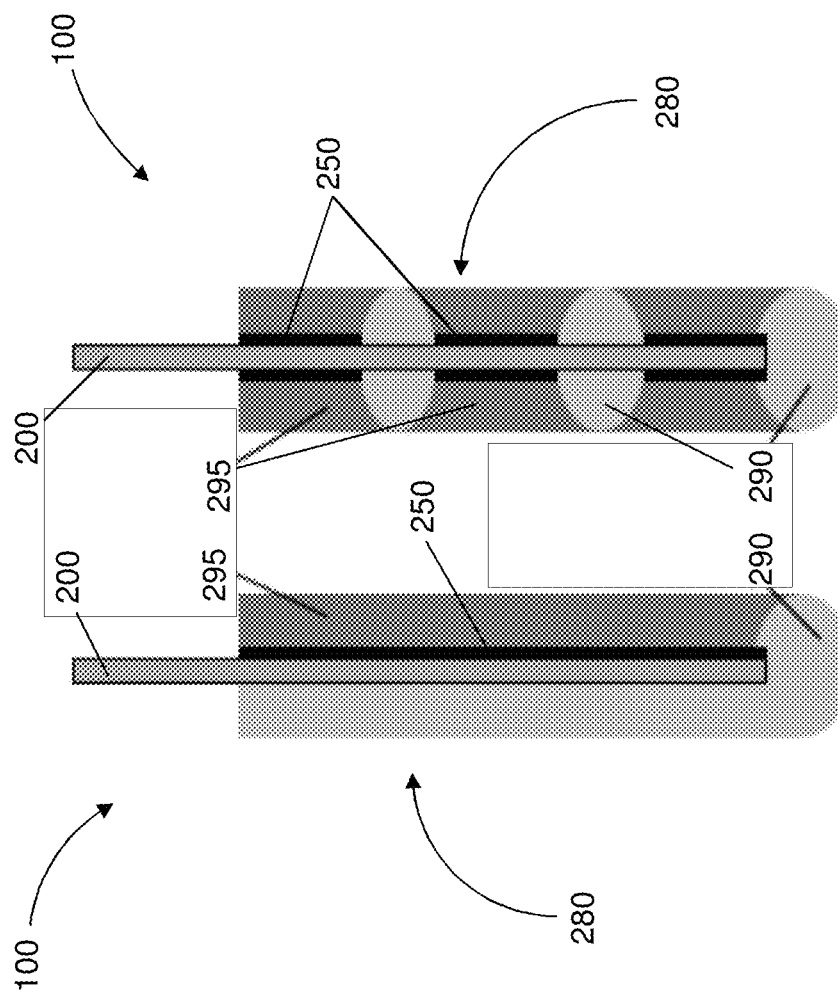
FIGS. 8A and 8B are partial views of a delivery system having a source electrode with at least one insulating member engaged therewith, the source electrode and at least one insulating member being encapsulated by a polymer matrix reservoir having a cargo contained therein.

Referring to FIG. 7, in some instances, the source electrode 200 (and/or the counter electrode) may be encapsulated in a gelatinous solid, such as, for example, a soft polymer matrix 280, that prevents injury from the insertion and extraction of the source electrode 200 (and/or the counter electrode). The polymer matrix 280 may also serve as a cargo reservoir 300 from where the therapeutic agent(s) may be mobilized. That is, the cargo 60 may be incorporated in the polymer matrix 280 such that, upon actuation of the electric field, the cargo 60 may diffuse out of the polymer matrix 280 and be delivered to the target site. FIGS. 8A and 8B illustrate the source electrode 200 having one or more insulating members 250 disposed thereabout such that both the source electrode 200 and the insulating members 250 are encapsulated in the polymer matrix 280. FIG. 8A shows a single insulating member 250 disposed longitudinally along the source electrode 200 such that the cargo 60 may be directed toward the target site. FIG. 8B shows a plurality of insulating members 250 engaged with the source electrode 200 such that various cargo delivery regions or zones are defined for delivering the cargo 60 to specific areas of the target site. In this regard, there may be a region or regions 290 of depleted cargo within the polymer matrix 280 and a normal region or regions 295 at some duration after actuation of the electric field to drive the cargo 60 toward the target site.

Figure 9:
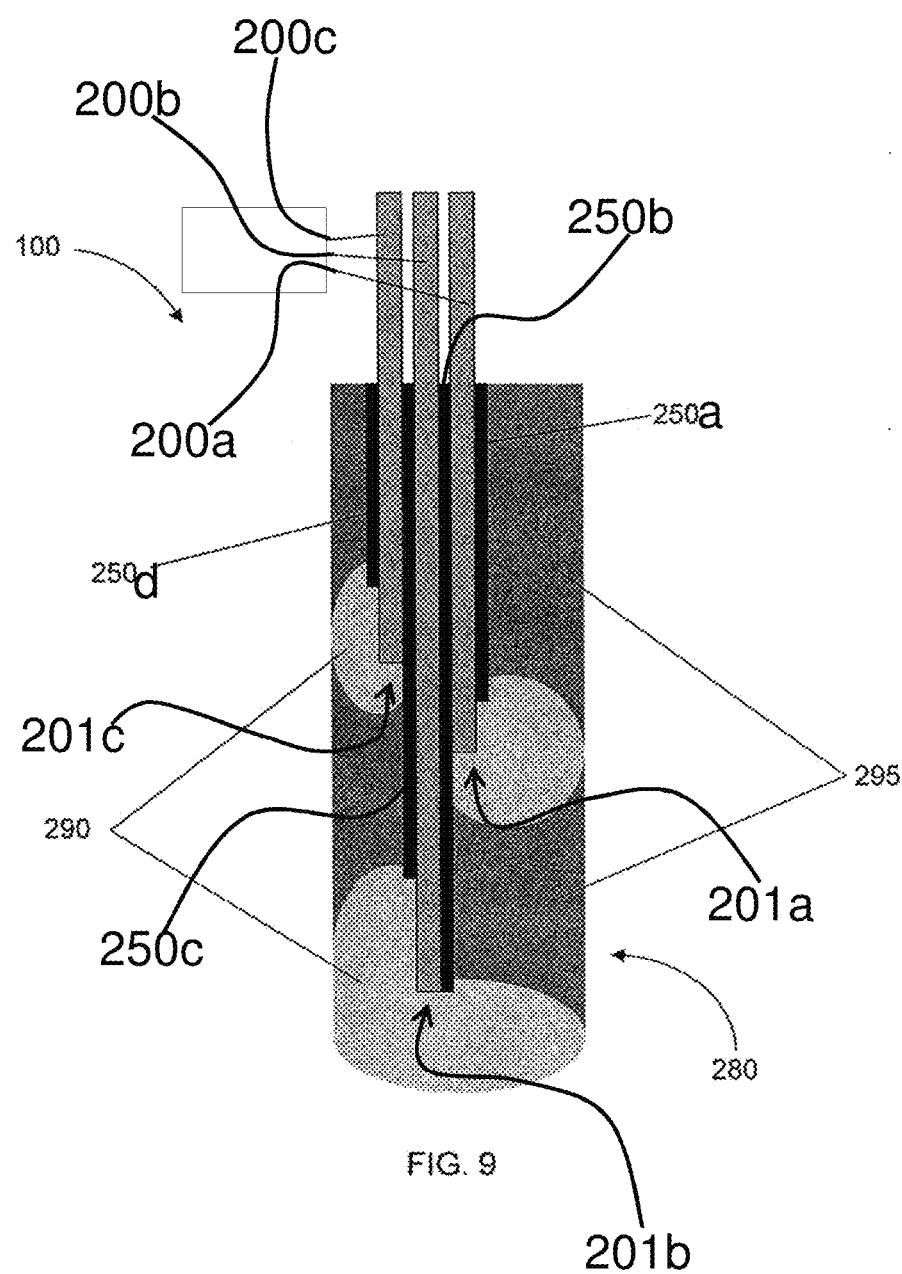
FIG. 9 is a partial view of a delivery system having a plurality of independently controlled source electrodes 200a, 200b and 200c and a plurality of insulating members 250a, 250b, 250c, and 250d arranged to provide controlled delivery zones, wherein the source electrodes and the insulating members are encapsulated in a polymer matrix, according to one embodiment of the present disclosure.

FIG. 9 illustrates an embodiment of the delivery system 100 similar to that of FIG. 5, wherein a plurality of independently controlled source electrodes and indicated by reference numbers 200a, 200b and 200c may be provided such that various target sites and/or regions may be targeted for delivery. As described previously, the length at which the source electrodes 200a, 200b and 200c terminate may alter (as shown by reference numbers 201a, 201b and 201c in FIGS. 2, 6 and 9) and the insulating members 250a, 250b, 250c and 250d may be provided to further control delivery of the cargo 60. In some instances, as shown in FIG. 9, the source electrodes 200a, 200b and 200c and insulating members 250a, 250b, 250c and 250d may be encapsulated in a gelatinous solid such as, for example, the polymer matrix 280 carrying the cargo 60 therewith. In this manner, there may be a region 290 of depleted cargo within the polymer matrix 280 and a normal region 295 at some duration after actuation of the electric field to drive the cargo 60 toward the target site.

In one embodiment, as illustrated in FIGS. 10 and 11, a catheter device, such as, for example, a balloon catheter 400 having a pair of expandable members 402 may be used to deliver the cargo 60 to the target site. The source electrode 200 may be serially disposed between the pair of expandable members 402, which are configured to occlude a target site. In this regard, the expandable members 402 may be used to enclose or occlude an intraluminal area before and/or after the source electrode 200, to limit the delivery of the cargo (e.g., therapeutic agent) to the area of interest. That is, the expandable members 402 may be in a relaxed state (FIG. 10) during positioning of the catheter and/or source electrode 200 proximate to the target site. Thereafter, the expandable members 402 may be inflated to an expanded state (FIG. 11) so as to contact a duct or other passageway 410 to enclose the target site such that the cargo delivery is isolated to the target site, thereby limiting exposure of healthy tissue to the cargo materials. In one embodiment, the delivery system 100 may include inflatable members 402, as schematically shown in FIGS. 10 and 11, which illustrate the distal end of the catheter device 400 with the expandable member 402 in its relaxed and inflated/expanded states, respectively. The catheter device 400 may include a guide wire for positioning the catheter device 400 near the target site. The term catheter as used in the present application is intended to broadly include any medical device designed for insertion into a body passageway to permit injection or withdrawal of fluids, to keep a passage open or for any other purpose. In other instances, an area to be treated may be occluded by blocking or damming an area using a balloon or a polymer cap or fibers (not shown).

Figure 12:
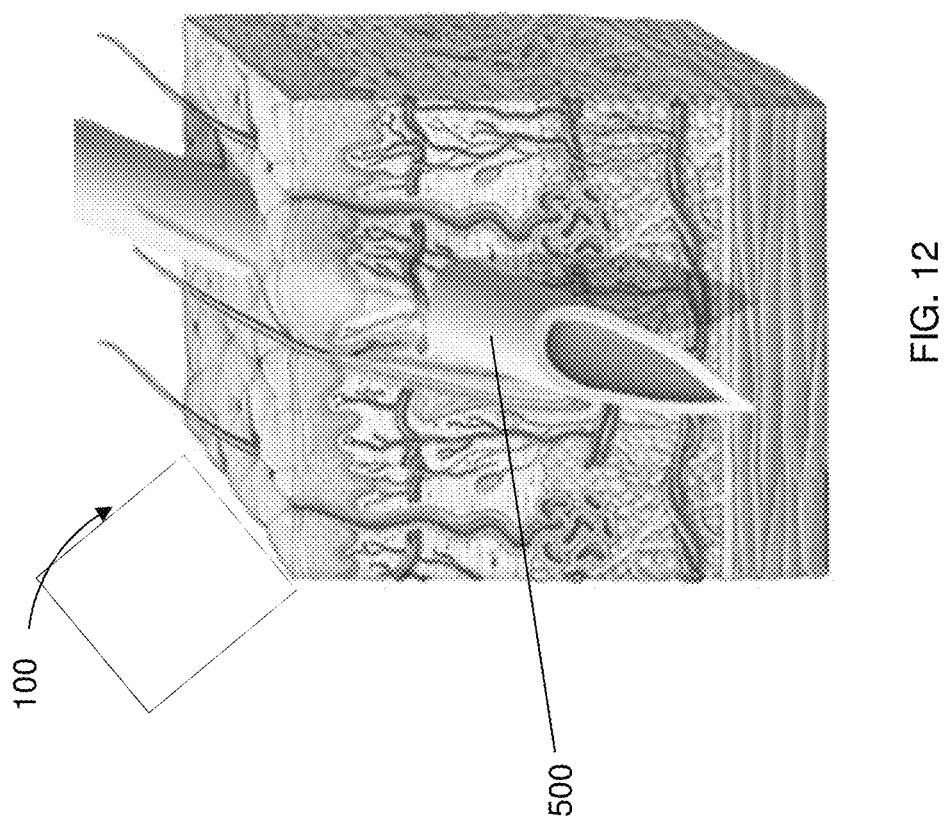
FIG. 12 is a partial view of a delivery system having a source electrode comprising a hollow tube needle member configured to deliver a cargo to a target site of internal body tissue, according to one embodiment of the present disclosure.

With reference to FIG. 12, in some embodiments of the present invention, placement of the cargo, such as the PRINT nanoparticles, may be achieved by using a hollow tube needle member 500 having an iontophoretic tip to facilitate distribution of the particles into the surrounding target site (tissue). In such embodiments, the needle tip may represent the source electrode 200, while the counter electrode is positioned internally or external to the body so as to create a voltage potential when a power supply is energized, as described previously with respect to iontophoretic techniques. Such a technique may be used for disease states including cancer (brain, prostate, colon, others), inflammation, damaged tissue 'rescue' situations (e.g. cardio/neuro/peripheral vascular), ocular diseases, rhinitis, and other applications. Furthermore, the hollow tube portion of the needle member 500 may serve as a reservoir for the cargo, wherein the needle member 500 may be connected to a port member (not shown) located externally such that the reservoir may be filled and/or refilled externally.

Referring to FIGS. 13A, 13B, 14, 15, and 16, one or more counter electrodes 500 may be provided with the delivery system 100, wherein the counter electrode 500 consists of a probe of opposite polarity to that of the source electrode 200 that completes the electrical circuit of the system. That is, in using embodiments of the present invention for iontophoretically enhanced drug delivery, a separate electrode of opposite polarity to the source electrode 200 is used in order to generate the potential gradient across the artery or other body tissue. In some instances, the counter electrode 500 may be positioned internally or otherwise external to the body such as on the patient's body (usually the skin) and may be attached using any known means, such as ECG conductive jelly. That is, placement of the source electrode 200 and the counter electrode 500 may be altered to fit the tissue location and disease state to be treated. For example, the source electrode 200 and the counter electrode 500 may be placed internally, externally or one internal and one external as long as appropriate electrical connection can be made. Internally placed electrodes can be proximal or distal in relation to each other and the tissue.

Figure 13B:
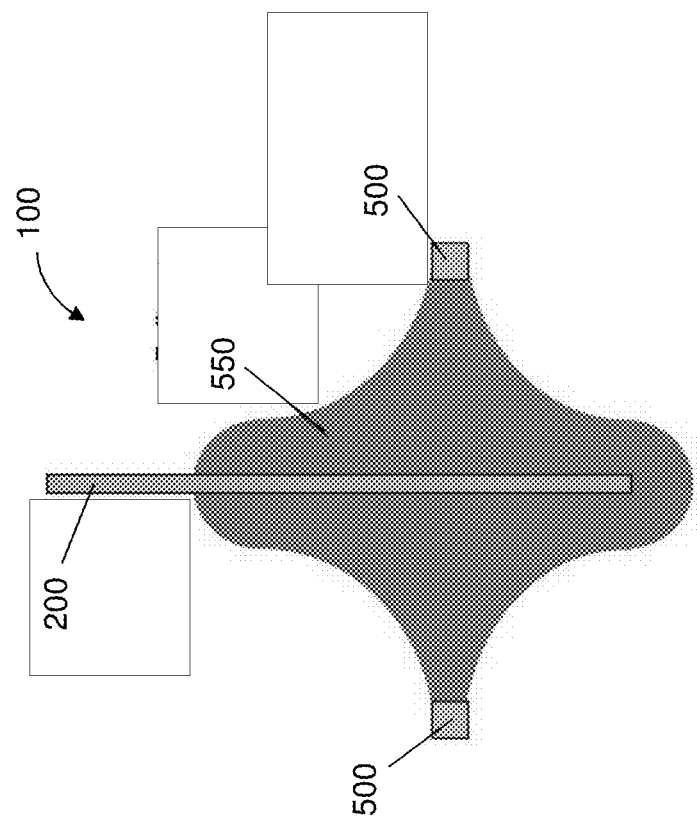
FIGS. 13A and 13B are partial views of a delivery system having a counter electrode positioned at various orientations with respect to the source electrode so as to target delivery of a cargo to a target site to predetermined in vivo locations.
Figure 13A:
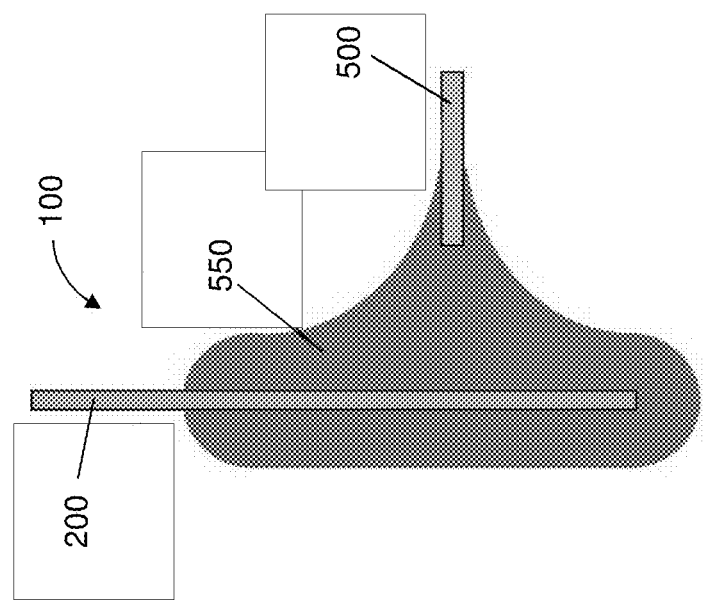

In some instances, as shown in FIGS. 13A and 13B, the counter electrode 500 may be designed to maximize movement of the cargo (e.g., the therapeutic agent) towards itself and away from the source electrode 200 so as to promote distinct and varied delivery zones 550. That is, the position of the counter electrode 500 may be manipulated to exert control over targeted delivery to specific in vivo locations. For example, as shown in the configuration of FIG. 13A, the counter electrode 500 may be positioned substantially perpendicularly with respect to the source electrode 200, whereas, as shown in the configuration of FIG. 13B, the counter electrode 500 may be concentrically positioned about the source electrode 200. Such configurations of the counter electrode 500 may lead to highly directional transport or broader transport bands, as dependent on the configuration and orientation with respect to the source electrode 200.

In some instances, the counter electrode 500 can have an ion selective membrane portion 502 for the movement of ions to and from the counter electrode 500. In some instances, the counter electrode 500 may have a coolant device 510 for use therewith to maintain the temperature of the counter electrode 500 and to minimize the potential for tissue burns, as illustrated in FIGS. 14-16. The coolant device 510 may be configured to allow a coolant substance 512 to flow at least partially about the counter electrode 500. In this regard, the membrane portion 502 may be positioned to prevent ions that may be part of the coolant substance 512 from interfering with the cargo, drug, or material to be deposited. In some embodiments, the coolant device 510 may include a perforated tubular structure 514 defining an aperture 516 to allow for release of the coolant around the counter electrode 500, as shown in FIG. 16. The coolant substance 512 may be, for example, water, an electrolyte solution, or gel-like substance that has a high heat capacitance to maintain cooler temperatures. In addition to performing a cooling function, the coolant substance 512 may allow for a continuous flow of electrolytes for maximum ion transfer into the tissue, and maintain pH levels around the counter electrode 500. A gelatinous membrane around the counter electrode 500 may also be utilized, to minimize pH changes occurring at the conducting surface and tissue interface. In one particular embodiment, the counter electrode 500 may be disposed between the insulator member 250 and the membrane portion 502 so as to improve delivery control of the cargo to the target site.

Embodiments of the present invention further comprise a reservoir (see, for example, FIGS. 1, 6-9, and 12) configured to store or otherwise carry the cargo such that the cargo may be at least partially disposed between the source electrode 200 and the counter electrode 500. In this manner, the cargo may interact with the electric field formed between the source electrode 200 and the counter electrode 500 so as to be delivered to the target site. The reservoir can be maintained as a solution, dispersion, emulsion or gelatinous solid, as previously describe with respect to FIGS. 7-9. The reservoir entraps the cargo (e.g., the therapeutic agent) until the application of a physical, chemical, or electrical stimulus. In one embodiment, the cargo reservoir may be located remotely from the source electrode 200 and may be connected to the source electrode 200 via a hollow conduit. In another embodiment, the reservoir and the source electrode 200 may be designed to be a single assembly. In any instance, it may be possible to refill the reservoir, either remotely or after every use. Large, medium, and small reservoirs may be provided to allow for directionality and concentration of the cargo (e.g., the therapeutic agent) issued to the tissue of interest.

In one particular embodiment of the present invention, the intraperitoneal cavity may serve as the drug reservoir. In this regard, the peritoneal cavity may be flooded with a cargo or drug of choice in an appropriate buffer. The source and counter electrodes 200, 500 may be positioned proximate to the target site of the pancreas, such as, for example, in a pancreatic duct and at an appropriate location or locations at the exterior of the pancreas near the tumor. Various arrangements of the source and counter electrodes may be implemented so that the cargo is positioned to interact with the electric field, upon actuation thereof, to drive the cargo to the target site of the pancreas. That is one, both, or neither of the electrodes may be positioned substantially within the pancreas. For example, both electrodes may be positioned exterior to the pancreas and on opposite sides thereof. In one particular example, one of the electrodes may be arranged as a wire mesh arrangement that can be positioned on and contact an exterior surface of the pancreas. A current may then be applied to drive the cargo (e.g., drug or therapeutic agent) from the peritoneal cavity to the pancreas and the site of the tumor. In another instance, the reservoir may be implanted in the intraperitoneal cavity such that the reservoir is provided remotely from the source electrode 200 and the counter electrode 500.

However, embodiments of the present invention may also be used in association with other cavities of the body, wherein at least some of these cavities are internal body cavities, while others are not. For example, the cargo may be delivered to the cranial cavity (brain cancers), the oral cavity (head and neck cancers, thyroid cancers), the thoracic cavity or mediastinum (thymus cancer, esophageal cancers and heart disease), the pleural cavity (lung cancers, cystic fibrosis, pulmonary fibrosis, emphysema, adult respiratory distress syndrome (ARDS), and sarcoidosis), the abdominopelvic cavity or peritoneal cavity (pancreatic cancer, liver cancers and metastases, stomach cancer, small bowel cancer, genital warts, inflammatory bowel diseases (Crohn's disease and ulcerative colitis), renal cancers and metastases, splenic cancers, and Hodgkin's disease), and the pelvic cavity (testicular cancer, prostate cancer, ovarian cancer fallopian tube, cervical cancer, endometrial cancer, uterine cancers, Kaposi's sarcoma, colorectal cancers, and urinary bladder cancer).

In order to apply a voltage potential across the source electrode 200 and the counter electrode 500, the source electrode 200 and the counter electrode 500 are in electrical communication. In this regard, the source electrode 200 and the counter electrode 500 are connected to a power source (not shown). In some instances, the power source may comprise a programmable power supply and function generator capable of generating both direct current and pulsed waveforms at various voltages and for various time intervals. The power source can generate the potential difference between the source electrode 200 and the counter electrode 500 necessary to induce electromigration and electroosmosis of the cargo (e.g., the therapeutic agent). A function generator allows for manipulation of the wave generated from the power source. Square, triangular, sawtooth, multistep wave forms may be used to drive a direct current through the source and counter electrodes 200, 500.

As described above, the disclosed iontophoretic techniques may take either an inside-out or an outside-in approach in driving the cargo toward the target site of tissue. That is, reverse iontophoretic techniques may be employed in all of the embodiments described hereinabove, and as described, for example, in Example 8. In this regard, the source electrode may be disposed exterior to a duct, organ, tissue, or target site, while the counter electrode is positioned within a duct, lumen, organ, etc. such that the cargo is driven from outside the target site inwardly toward the target site.

Many modifications and other embodiments of the invention will come to mind to one skilled in the art to which this invention pertains having the benefit of the teachings presented in the foregoing description; and it will be apparent to those skilled in the art that variations and modifications of the present invention can be made without departing from the scope or spirit of the invention. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The following examples are presented by way of illustration, not by way of limitation.

EXPERIMENTAL

Example 1: Delivery of Rhodamine 6G Dye into Agarose Phantoms

Figure 17B:
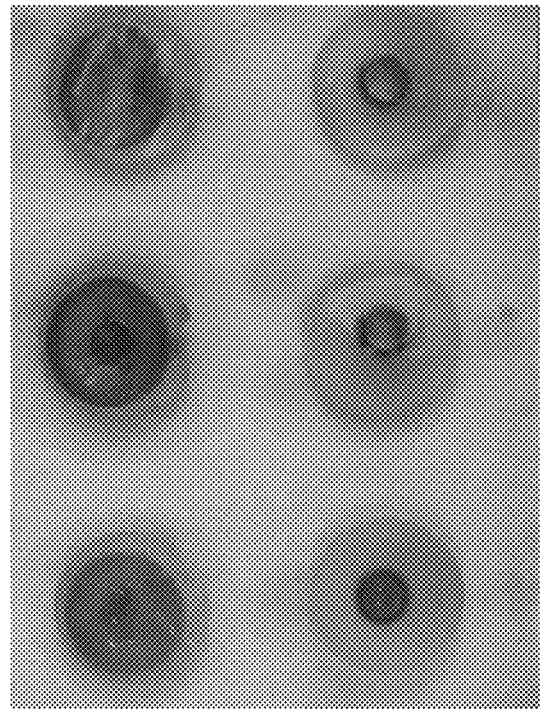
FIGS. 17A and 17B are images illustrating an experimental implementation of a delivery system in accordance with one aspect of the present disclosure.
Figure 17A:
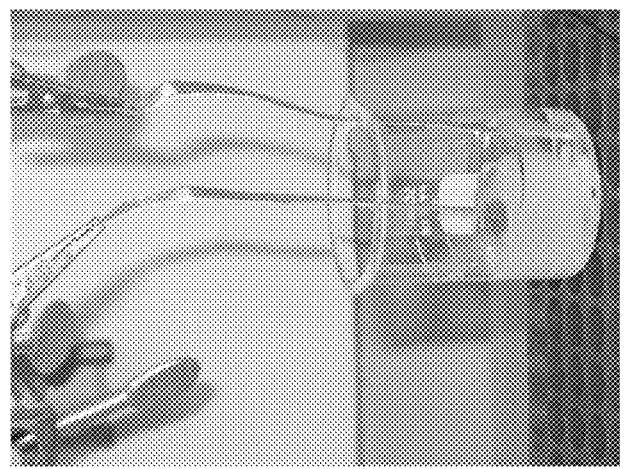

A cylindrical tube of 2% (w/v) agarose gel in deionized (D.I.) water was fabricated as a phantom with an outer diameter (o.d.)=2.5 cm and length ~3-4 cm. A concentric reservoir for holding the dye (o.d=0.8 cm, length ~2 cm) was cored out from the top surface along the longitudinal axis of the gel cylinder. Electrodes were fabricated out of aluminum foil (width ~0.5 cm, length ~15 cm, thickness ~0.1 cm). A solution of 0.5% Rhodamine 6G in D.I. water was used to model the delivery of a small molecule drug. The dye was filled inside the cored reservoir in the agarose phantom and the source electrode (anode, in this case) was inserted into the dye reservoir. The other end of the anode was hooked to a DC power source with an alligator clip. The agarose phantom was immersed in a beaker containing 0.25×PBS solution, as shown in FIG. 17A. The cathode, a second piece of aluminum foil, was placed in the PBS beside the agarose phantom and hooked up to the DC power source. In the negative control, passive diffusion of the dye was allowed without any passage of current for 10 minutes. In the experimental condition, a constant current of 5 mA (voltage ~9.5V) was driven through the electrodes for the same duration (10 minutes). As shown in FIG. 17B, to characterize the extent of iontophoretic transport, cross-sections of the agarose phantom were taken every 0.5 cm along the length. The radial transport of the dye from the edge of the cored reservoir was quantified. In the negative control (0 mA) dye was localized to the inner wall of the reservoir, while in the experimental condition (5 mA) the dye spread radially to the edge of the agarose phantom.

Figure 18B:
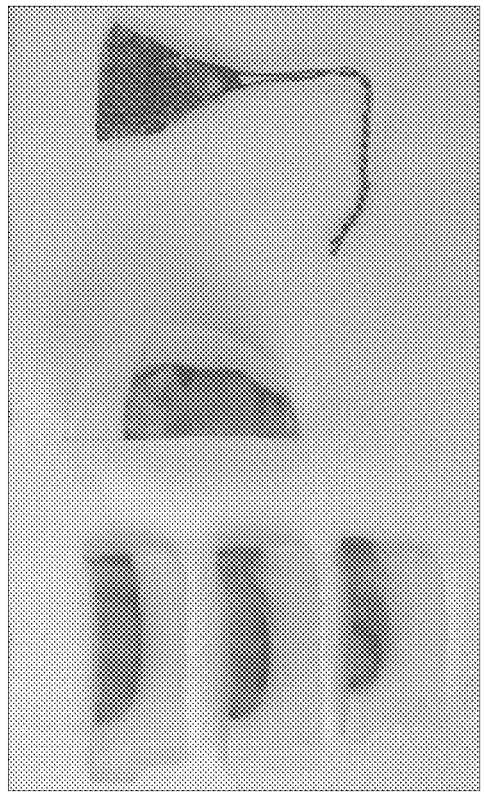
FIGS. 18A and 18B are images illustrating an experimental implementation of a delivery system in accordance with another aspect of the present disclosure.
Figure 18A:
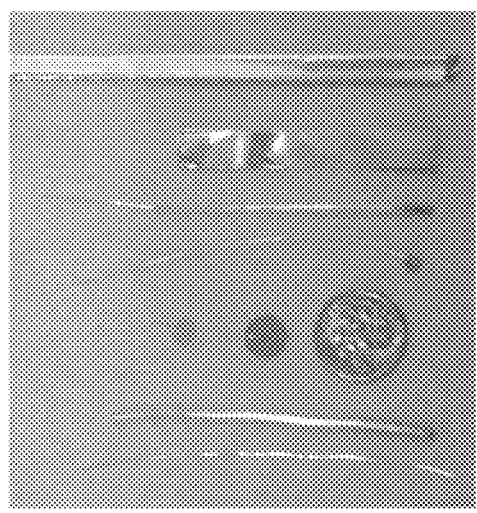

Example 2: Unshielded Electrode Configurations for Control Over Targeted Delivery to Specific In Vivo Locations Unshielded electrode configurations were developed for demonstrating control over delivery to specific in vivo locations. These include electrodes fabricated out of metal wire (silver, silver chloride), metal foil (silver, platinum, aluminum) and wire mesh (aluminum), as shown in FIGS. 18A and 18B. These are representative examples, and similar designs can be fabricated with variations in size, material and additional enhancements or refinements to the basic configuration. The advantages of wire and foil electrodes shown FIG. 18A are: simplicity and ease of use, flexibility for insertion into tiny orifices and ducts, precise control over size and potential for miniaturization. Their primary limitation is their tendency for hydrolysis of the conducting fluid medium. Silver electrodes are also susceptible to oxidation, while silver chloride electrodes can get reduced to metallic. As shown in FIG. 18B, wire mesh electrodes can be fabricated either in a stent configuration for intra-luminal placement, or as a patch or net configuration for placement on the outside surface of an organ or target tissue. Such a configuration may provide greater control over the surface area of delivery, as well as better heat flow to reduce the potential for tissue burns. Additionally, these may be fabricated from conducting polymers or coated with biodegradable polymers to create designs that are highly conformable to organ surface characteristics and geometrical contours.

Figure 19C:
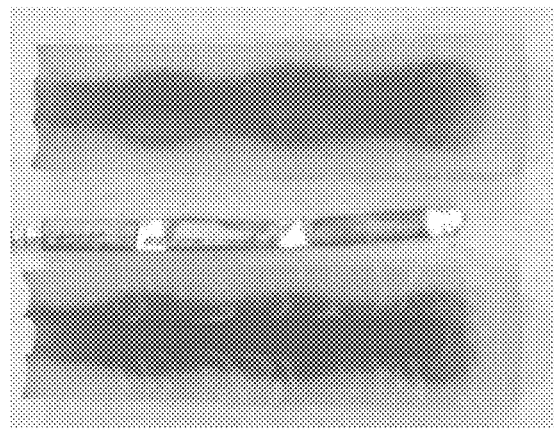
FIGS. 19A-19C are images illustrating an experimental implementation of a delivery system in accordance with yet another aspect of the present disclosure.
Figure 19B:
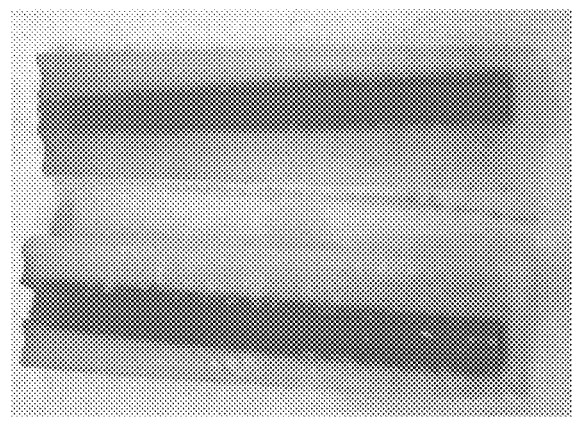
Figure 19A:

Example 3: Insulated Electrode Configurations for Control Over Targeted Delivery to Specific In Vivo Locations An insulated electrode was developed to demonstrate control over targeted delivery to specific in vivo locations. By insulating a portion of the electrode surface, it is possible to control the delivery to the tissue or organ systems in a well defined fashion. For example, the flux of drug or particles will be attenuated corresponding to the insulated areas of the electrode. Aluminum foil was folded into a long rectangular shape of appropriate dimensions (length ~10 cm, width ~0.4 cm, thickness ~0.1 cm). Insulating tape (width ~1 cm) was wrapped around the foil in alternating sections. This insulated electrode was immersed in the central reservoir of an agarose phantom (2% agarose w/v in deionized water), as shown in FIG. 19A. A solution of 0.5% Rhodamine 6G in D.I. water was used to model the delivery of a small molecule drug. The dye was filled inside the cored reservoir in the agarose phantom and the insulated source electrode (anode, in this case) was inserted into the dye reservoir. The agarose phantom was immersed in a beaker containing 0.25×PBS solution. A bare aluminum foil electrode served as a cathode, and was placed in the PBS beside the phantom. Both electrodes were hooked to a DC power source with alligator clips. In the negative control, passive diffusion of the dye was allowed without any passage of current for 10 minutes. In the experimental condition, a constant current of 5 mA (voltage ~9.5V) was driven through the electrodes for the same duration (10 minutes). To characterize the extent of iontophoretic transport, the agarose phantom was sectioned longitudinally. A difference is seen in the extent of transport from the sections of the phantom exposed to the unshielded sections of the electrode, as compared to diffusion from the passive control, as shown in FIGS. 19B and 19C, respectively.

Example 4: Electrode Configurations with Built-In Drug Reservoirs

Figure 20B:
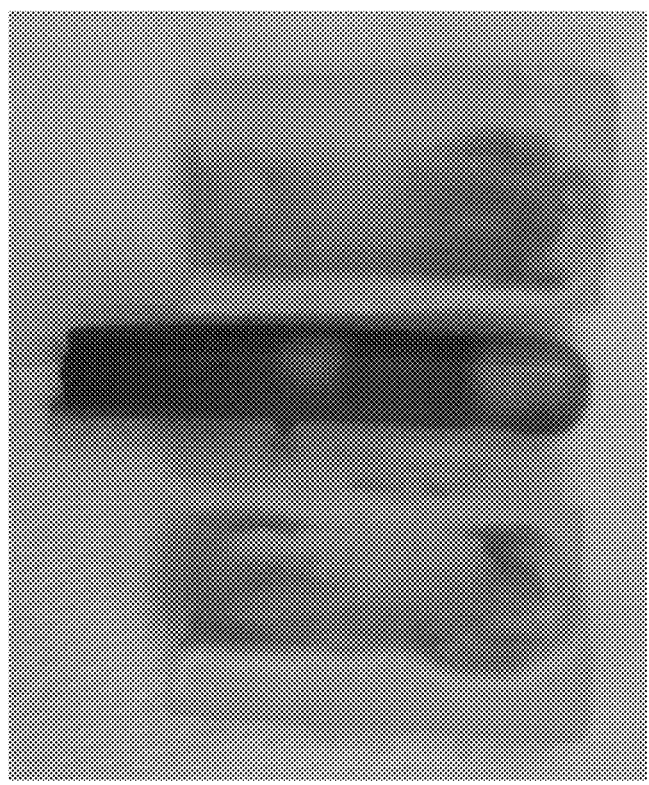
FIGS. 20A and 20B are images illustrating an experimental implementation of a delivery system in accordance with still another aspect of the present disclosure.
Figure 20A:
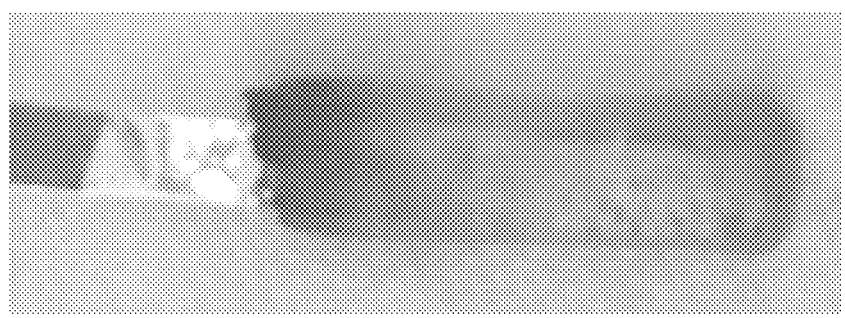

Since it may not be possible to confine the drug to be delivered within a localized cavity or lumen in the target tissue, electrodes with built-in drug reservoirs were developed. Such examples were fabricated by encapsulating insulated foil electrodes described earlier within an agarose gel matrix. The agarose gel containing the 0.5% Rhodamine 6G solution, serving as a model drug, was first poured into a glass test-tube of diameter 1.2 cm. The insulated electrode was then inserted into the gel solution. The gel was allowed to solidify, and the electrode was extracted by breaking the test tube. An agarose gel phantom with a central reservoir of inner diameter ~1.5 cm was prepared. This electrode was then inserted into the phantom and tested for iontophoretic delivery at a constant current of 5 mA for 10 minutes. The results show zones of controlled delivery through the gel that are visible under short wave UV light, as shown in FIG. 20B. FIG. 20A shows the electrode having the built-in drug reservoir being at least partially depleted of the model drug after completion of the experiment. Similar results were also seen in transport through muscle and fat tissue.

Example 5: Delivery of Dye into Muscle Tissue (Chicken Breast)

Figure 21:
FIG. 21 is an image illustrating an experimental implementation of a delivery system in accordance with another aspect of the present disclosure.

A soft-gel electrode was fabricated from 2% (w/v) agarose gel containing 5% Rhodamine 6G solution in D.I. water by casting the gel in a test tube (o.d.=13 mm and length ~25 mm) with an aluminum foil electrode inserted along the central axis. Chicken breast was chosen as a representative tissue to demonstrate iontophoretic delivery in accordance with one embodiment of the present delivery system. A cylindrical core was removed from the center of the tissue sample to produce a drug reservoir of o.d.=15 mm. The soft-gel electrode was then placed in the reservoir inside the tissue sample and the source electrode (anode, in this case) was hooked to a DC power source with an alligator clip. The tissue sample was immersed in a beaker containing deionized water. The cathode, a regular aluminum foil electrode without seal, was placed in the PBS beside the tissue sample and hooked up to the DC power source. In the negative control, passive diffusion of the dye into the tissue was allowed without any passage of current for 30 minutes. In the experimental condition, a constant current of 10 mA (voltage ~1.4 V) was driven through the electrodes for the same duration (30 minutes). To characterize the extent of iontophoretic transport, cross-sections of the tissue sample were taken every 0.5 cm along the depth of the sample, as shown in FIG. 21. The radial transport of the dye from the edge of the drug reservoir was quantified. As shown in the top row of FIG. 21, in the negative control (0 mA), the dye was localized to the inner wall of the reservoir. As shown in the bottom row of FIG. 21, in the experimental condition (10 mA), the dye spread in a radial direction into the tissue to a distance of ~5 mm from the edge of the reservoir.

Example 6: Delivery of Dye into Adipose Tissue (Bovine)

Figure 22:
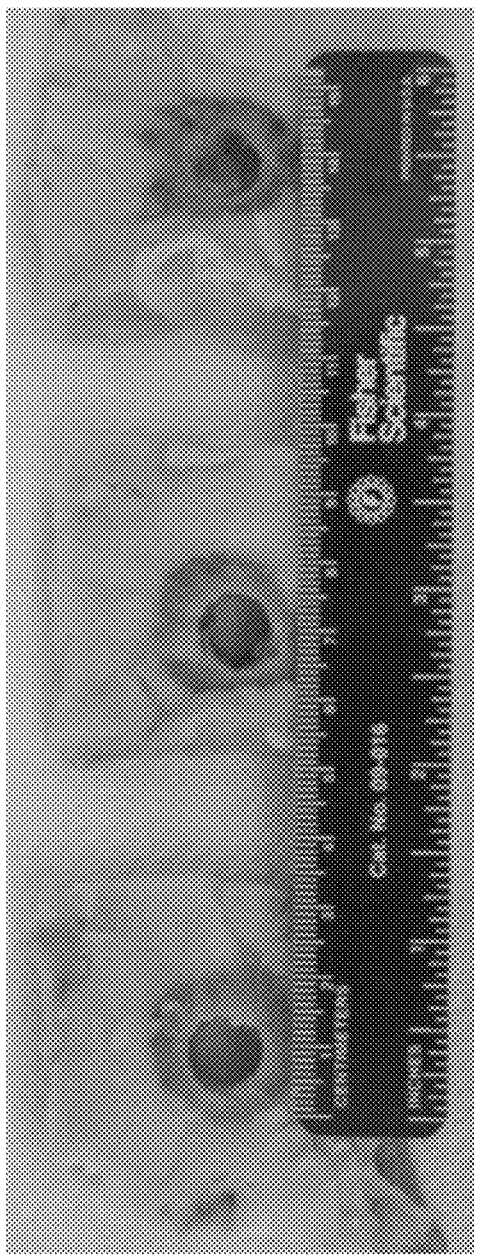
FIG. 22 is an image illustrating an experimental implementation of a delivery system in accordance with still yet another aspect of the present disclosure.

Bovine fat was chosen as another representative tissue to demonstrate iontophoretic delivery. A cylindrical core was removed from the center of the tissue sample to produce a drug reservoir of o.d.=15 mm. A soft-gel electrode similar to the one described earlier, but with platinum foil (0.5 mm thick) as the source electrode, was then placed in the reservoir at the center of the tissue sample and was hooked to a DC power source with an alligator clip. The tissue sample was immersed in a beaker containing deionized water (mimicking filling the peritoneal cavity). A silver chloride electrode directly inserted into the tissue sample served as the cathode and was hooked up to the DC power source. In the negative control, passive diffusion of the dye into the fat tissue was allowed without any passage of current for 30 minutes. In the experimental condition, a constant voltage of 20 V was applied between the electrodes for the same duration (30 minutes). The current was allowed to increase from 5-15 mA to maintain constant potential difference. To characterize the extent of iontophoretic diffusion, cross-sections of the tissue sample were taken every 0.5 cm along the depth of the sample. The radial diffusion of the dye from the edge of the drug reservoir was quantified. In the negative control (0 V) dye was localized to the inner wall of the reservoir (not shown). In the experimental condition (20 V), a maximum penetration depth of ~8 mm from the edge of the reservoir was achieved, as shown in FIG. 22.

Figure 23B:
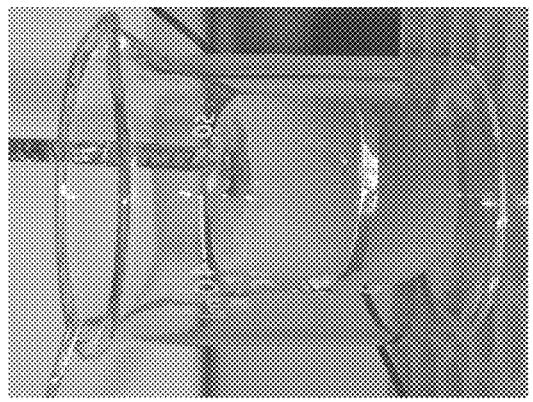
FIGS. 23A and 23B are images illustrating an experimental implementation of a delivery system in accordance with one aspect of the present disclosure.
Figure 23A:
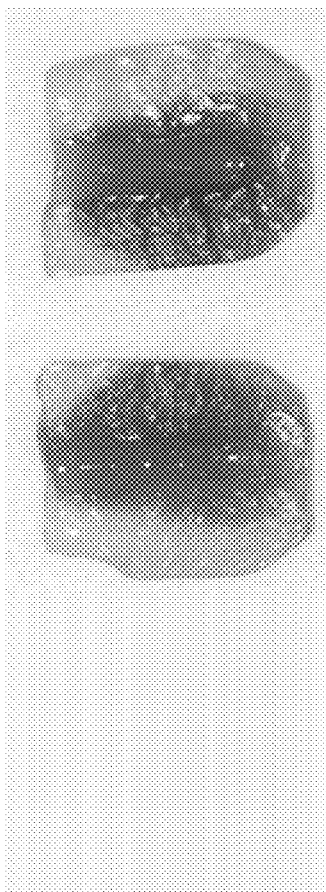

Example 7: Placement of Counter Electrodes for Control Over Targeted Delivery to Specific In Vivo Locations As described previously, the position of the counter electrode may be manipulated to exert control over targeted delivery to specific in vivo locations. In this example, two possible configurations are illustrated in FIGS. 23A and 23B, which correspond to the configuration of FIGS. 13A and 13B, respectively. In the first configuration, the counter electrode was placed in direct point contact with the outside surface of the agarose gel phantom. In the second configuration, the counter electrode was wrapped around the midsection of the gel, as shown in FIG. 23B. The agarose phantoms were the same as those used in Example 1, and a constant current of 5 mA was allowed to flow through the electrodes for 10 minutes. In the first configuration, highly directional diffusion was seen on the side of the agarose phantom with direct counter electrode contact, as shown in FIG. 23A. In the second configuration, a broader diffusion band is seen around the midsection, demonstrating greater diffusivity towards the counter electrode wrapped around the phantom.

Example 8: Delivery of Dye Using Reverse Iontophoresis

Figure 24B:
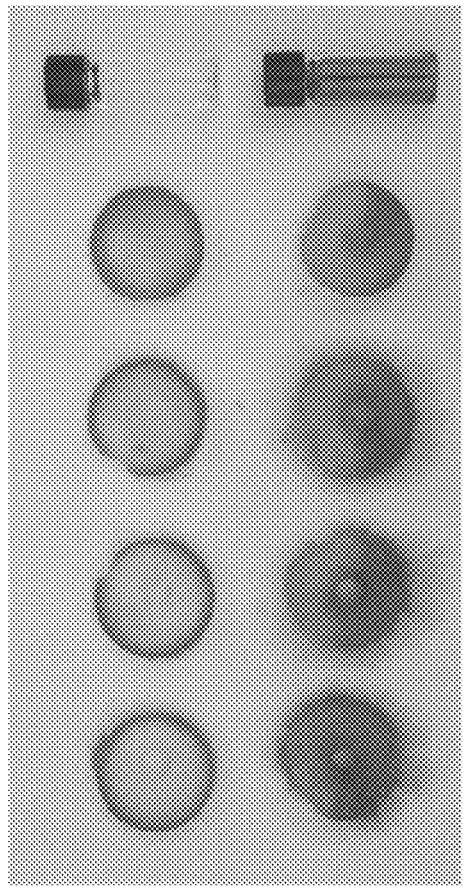
FIGS. 24A and 24B are images illustrating an experimental implementation of a delivery system in accordance with yet another aspect of the present disclosure.
Figure 24A:
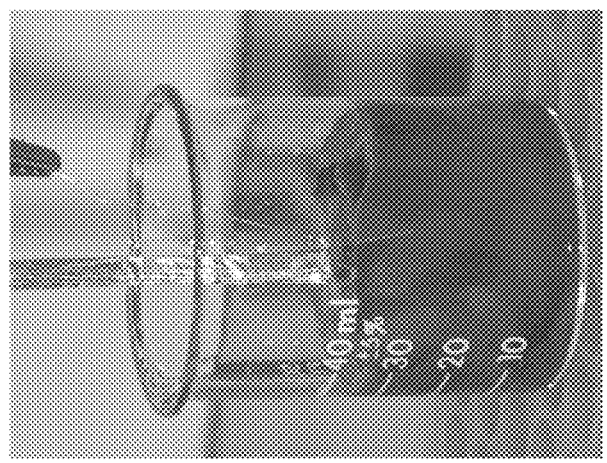

The ability to extract a small molecule from the surrounding medium (like filling the peritoneal cavity) into a reservoir located inside an agarose phantom was demonstrated by employing the principle of reverse iontophoresis. To allow diffusion from the outside surface of the gel to the central reservoir, the phantom was placed in a solution of Rhodamine 6G in deionized water. For this application, the polarity of the electrodes was switched, with the counter electrode being placed in the central drug reservoir, while the source electrode was placed in the dye solution outside the gel, as shown in FIG. 24A. The electrodes were then hooked to a DC power source with an alligator clip. In the negative control, the gel was soaked in the dye solution without any passage of current for 10 minutes. In the experimental condition, a constant current of 5 mA (voltage ~9.5V) was driven through the electrodes for the same duration (10 minutes). To characterize the extent of reverse iontophoretic diffusion, cross-sections of the agarose phantom were taken every 0.5 cm along the length. The radial diffusion of the dye from the outside surface of the gel to the inside edge of the central reservoir was quantified. In the negative control (0 mA) dye was localized to the outer wall of the gel, as shown in the top row of FIG. 24B. In the experimental condition (5 mA) the dye spread radially toward the central reservoir and collected there, as shown in the bottom row of FIG. 24B. In the experimental condition, the total volume of dye accumulated in 10 minutes was sufficient to fill up a 3 mL glass vial, as shown in the bottom vial of FIG. 24B. This example demonstrates the potential of the invention for delivering drug molecules from the outside surface of an organ to the inner core. It also demonstrates an application requiring the extraction of a toxin from the target tissue into a central reservoir from which it can be safely and easily extracted.

Figure 25:
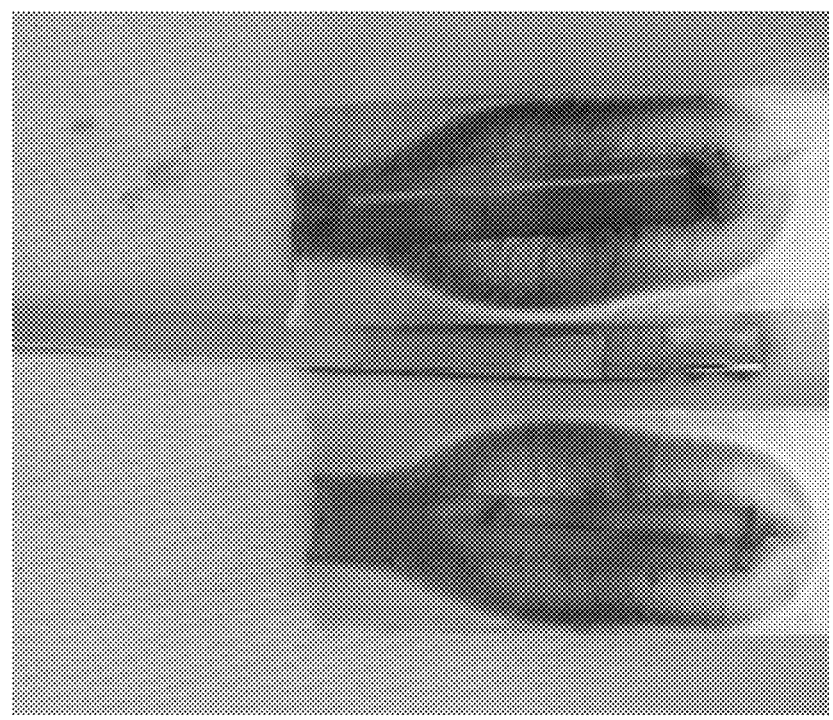
FIG. 25 is an image illustrating an experimental implementation of a delivery system in accordance with one aspect of the present disclosure.

Example 9: Variable Delivery of Rhodamine 6G Dye into Agarose Phantoms Using Independently Controlled Electrodes An assembly of two independently-powered, insulated electrodes was developed to demonstrate variable controlled delivery, as described previously. By allowing independent control over parameters for iontophoretic delivery such as current, voltage and time, we were able to demonstrate variable delivery zones at two distinct sites within the same lumen. Two insulated aluminum foil electrodes similar to the one shown in Example 3 above, were combined into a single assembly according to the schematic shown in FIG. 5. The insulated double-electrode assembly was immersed in the central reservoir of an agarose phantom (2% agarose w/v in deionized water). A solution of 0.5% Rhodamine 6G in D.I. water was used to model the delivery of a small molecule drug and was filled inside the cored reservoir in the agarose phantom. The agarose phantom was immersed in a beaker containing 0.25×PBS solution. A pair of bare aluminum foil electrodes served as cathodes, and were placed in the PBS beside the phantom. Both sets of electrodes were hooked to two independent DC power sources with alligator clips. In the negative control, passive diffusion of the dye was allowed without any passage of current for 5 minutes. In the experimental condition, one electrode was set for a constant current of 5 mA, while the other was operated at a constant voltage of 20 V. Duration of delivery was held constant at 5 minutes, but as noted earlier, all of the above parameters can be independently controlled. To characterize the extent of iontophoretic diffusion, the agarose phantom was sectioned longitudinally. Under UV light, a difference is seen in the extent of diffusion from the sections of the phantom exposed to the uninsulated sections of both electrodes in the assembly, as shown in FIG. 25. For example, the bottom electrode shows uniform diffusion at the bottom of the well, whereas the uninsulated section of the top electrode shows more diffusion on the bare (anterior) side as opposed to the insulated (posterior) side. This example demonstrates that a similar electrode assembly can be used to control the location and extent of delivery at multiple proximal sites within the same lumen or its branches. This may be particularly useful in targeted delivery to metastatic tumors within the same organ that can be accessed through a common ductal or vascular network.

Figure 26B:
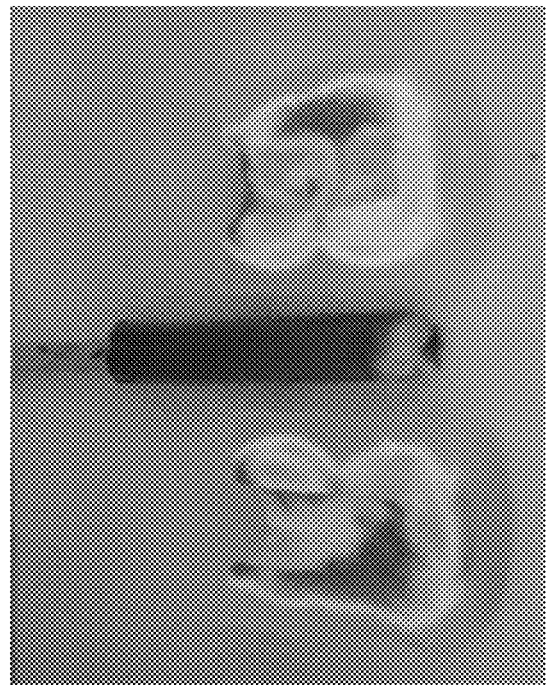
FIGS. 26A and 26B are images illustrating an experimental implementation of a delivery system in accordance with yet another aspect of the present disclosure.
Figure 26A:
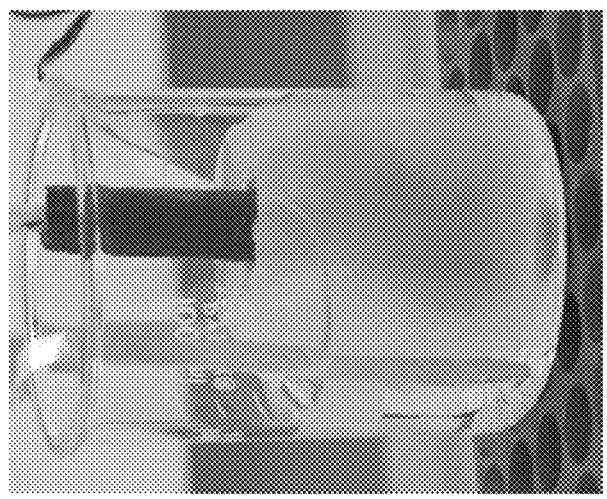

Example 10: Variable Delivery of Rhodamine 6G Dye into Agarose Phantoms Using Independently Controlled Electrodes with Built-In Drug Reservoir A variation of the double-electrode assembly previously described in Example 9 was developed with a built-in drug reservoir. The insulated double-electrode assembly was immersed in a test-tube of 2% agarose gel containing a 5 mg aqueous solution of Rhodamine 6G. The soft-gel electrode assembly was then inserted into an 2% agarose phantom having a cored out central cavity (diameter: 1.5 mm). The agarose phantom was immersed in a beaker containing 0.25×PBS solution, as shown in FIG. 26A. Two bare aluminum foil electrodes served as cathodes, and were placed in the PBS beside the phantom. Both sets of electrodes were hooked to two independent DC power sources with alligator clips. In the negative control, passive diffusion of the dye was allowed without any passage of current for 7 minutes. To demonstrate independent control of both electrodes, one electrode was set for a constant current of 5 mA for 5 minutes, while the other was operated at a constant current of 15 mA for 7 minutes. To characterize the extent of iontophoretic diffusion, the agarose phantom was sectioned longitudinally. Under UV light, a difference is seen in the extent of diffusion from the sections of the phantom exposed to the uninsulated sections of both electrodes in the assembly, as shown in FIG. 26B. Depletion of the dye is seen from the areas of the gel exposed to uninsulated tips of the electrodes. Furthermore, two distinct delivery zones can be seen resulting from the two independently controlled electrodes.

Example 11: Delivery of Doxorubicin into Agarose Phantoms

Figure 27:
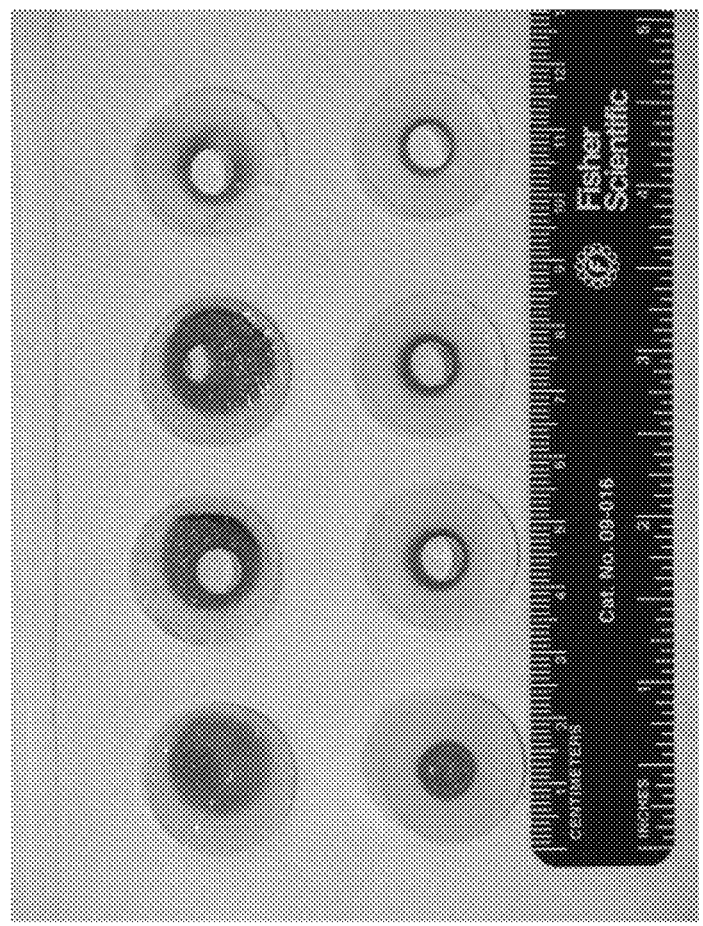
FIG. 27 is an image illustrating an experimental implementation of a delivery system in accordance with one aspect of the present disclosure.

A cylindrical tube of 2% (w/v) agarose gel in deionized (D.I.) water was fabricated as a phantom with an outer diameter (o.d.)=2.5 cm and length ~3-4 cm. A concentric reservoir for holding the dye (o.d=0.8 cm, length ~2 cm) was cored out from the top surface along the longitudinal axis of the gel cylinder. Electrodes were fabricated out of platinum foil (width ~0.25 cm, length ~3 cm, thickness ~0.05 cm). A solution of 0.25% Doxorubicin in 4.875% DMSO and 94.875% DI water was used to model the delivery of a small molecule drug. The dye was filled inside the cored reservoir in the agarose phantom and the source electrode (anode, in this case) was inserted into the dye reservoir. The other end of the anode was hooked to a DC power source with an alligator clip. The agarose phantom was immersed in a beaker containing DI water. The cathode, a second piece of platinum foil, was placed in the PBS beside the agarose phantom and hooked up to the DC power source. In the negative control, passive diffusion of the dye was allowed without any passage of current for 5 minutes. In the experimental condition, a constant current of 5 mA (voltage ~9.5V) was driven through the electrodes for the same duration (5 minutes). As shown in FIG. 27, to characterize the extent of iontophoretic diffusion, cross-sections of the agarose phantom were taken every 0.5 cm along the length. The radial diffusion of the dye from the edge of the cored reservoir was quantified. In the negative control (0 mA) dye was localized to the inner wall of the reservoir (bottom row), while in the experimental condition (5 mA) the dye spread radially to the edge of the agarose phantom (top row).

Figure 28B:
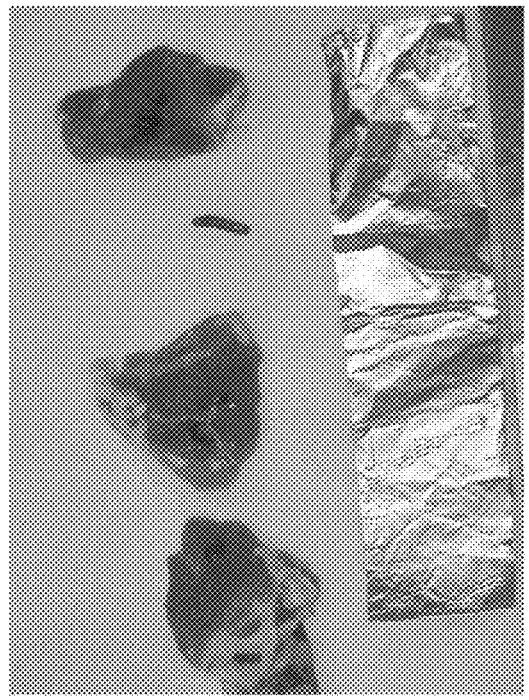
FIGS. 28A and 28B are images illustrating an experimental implementation of a delivery system in accordance with one aspect of the present disclosure.
Figure 28A:
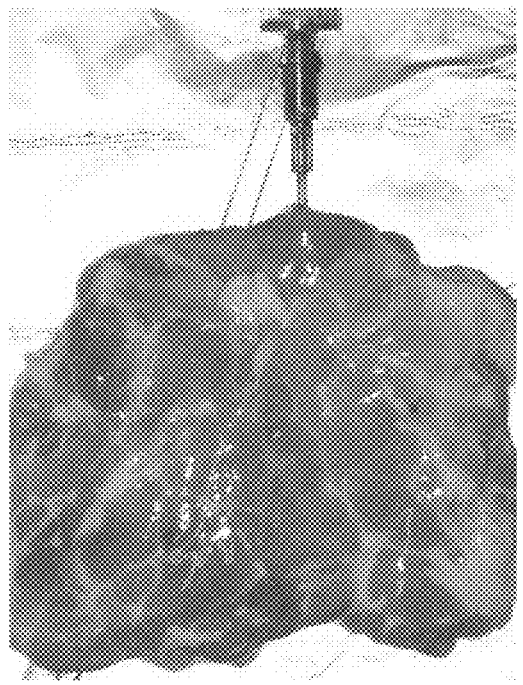

Example 12: Injection of Rhodamine 6G into Pancreatic Duct and Placement of Electrodes on Outer Surface of Pancreas As shown in FIG. 28A, Liquified 2% (w/v) agarose gel containing 0.5% Rhodamine 6G solution in D.I. water was injected into the pancreas duct through a 18G IV catheter, where it solidified upon contact. The source electrode, made of aluminum foil, was placed on one side of the pancreas, and the counter electrode, made of aluminum foil, was placed on the opposite side of the pancreas. The electrodes were hooked to a DC power source with alligator clips. The tissue sample was immersed in a beaker of DI water. In the experimental condition, a constant current of 5 mA (voltage 2.4 V) was driven through the electrodes for the same duration (30 minutes). To characterize the extent of iontophoretic diffusion, cross-sections of the tissue sample were taken every 0.5 cm along the depth of the sample, as shown in FIG. 28B. The radial diffusion of the dye from the edge of the drug reservoir was quantified. In the experimental condition (5 mA), the dye spread in a radial direction into the tissue to a distance of ~3 mm from the edge of the reservoir.

Example 13: Delivery of Dye into Pancreas Using Flat Electrodes

Figure 29:
FIG. 29 is an image illustrating an experimental implementation of a delivery system in accordance with another aspect of the present disclosure.

A soft-gel source electrode was fabricated from Liquified 2% (w/v) agarose gel containing 0.5% Rhodamine 6G solution in D.I. water by casting the gel in a Petri dish with an aluminum foil electrode inserted on top of gel. The source electrode was placed on one side of the pancreas, and the counter electrode was placed on the opposite side of the pancreas. The electrodes were hooked to a DC power source with alligator clips. The tissue sample was immersed in a beaker of DI water. In the experimental condition, a constant current of 5 mA (voltage ~2.4 V) was driven through the electrodes for the same duration (30 minutes). As shown in FIG. 29, in the experimental condition (5 mA), the dye moved from the agarose source electrode into the tissue.

Example 14: Delivery of Dye Through Pancreatic Duct Using Probe Electrode

Figure 30A:
FIGS. 30A-30C are images illustrating an experimental implementation of a delivery system in accordance with another aspect of the present disclosure.
Figure 30C:
Figure 30B:

A soft-gel source electrode was fabricated from Liquified 2% (w/v) agarose gel containing 0.5% Rhodamine 6G solution in D.I. water by casting the gel in a test tube (o.d.=5 mm and length ~25 mm) with platinum wire inserted along the central axis. The soft-gel source electrode was probed into the pancreatic duct, and the counter electrode, made of platinum foil, was placed on the outer surface of the pancreas, as shown in FIG. 30A. The electrodes were hooked to a DC power source with alligator clips. The tissue sample was immersed in a beaker of DI water. In the negative control, passive diffusion of the dye into the tissue was allowed without any passage of current for 30 minutes. In the experimental condition, a constant current of 20 mA (voltage ~9.2 V) was driven through the electrodes for 30 minutes. To characterize the extent of iontophoretic diffusion, cross-sections of the tissue sample was taken every 1 cm along the depth of the sample. As shown in FIG. 30B, in the experimental condition (20 mA), the dye moved from the agarose source electrode into the tissue. As shown in FIG. 30C, in the negative control (0 mA), the dye was localized to the inner wall of the pancreatic duct. In the experimental condition (20 mA), the dye spread in a radial direction into the tissue to a distance of ~3 mm from the edge of the reservoir.

Example 15: Delivery of PRINT® Nanoparticles into Agarose Phantoms

Figure 31B:
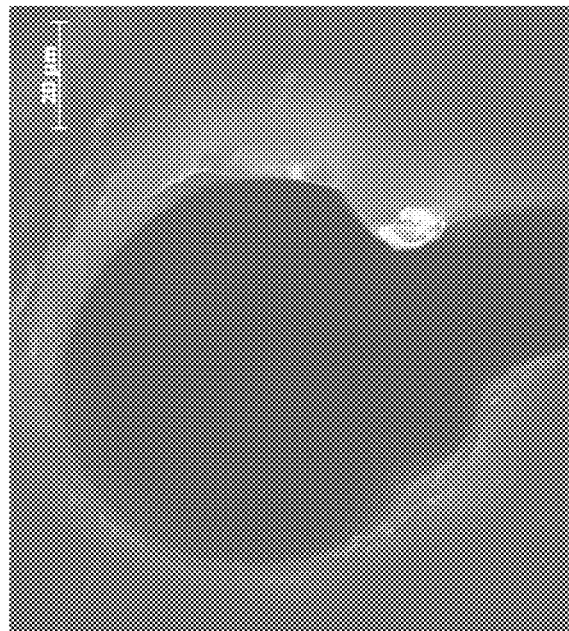
FIGS. 31A and 31B are images illustrating an experimental implementation of a delivery system in accordance with one aspect of the present disclosure.
Figure 31A:
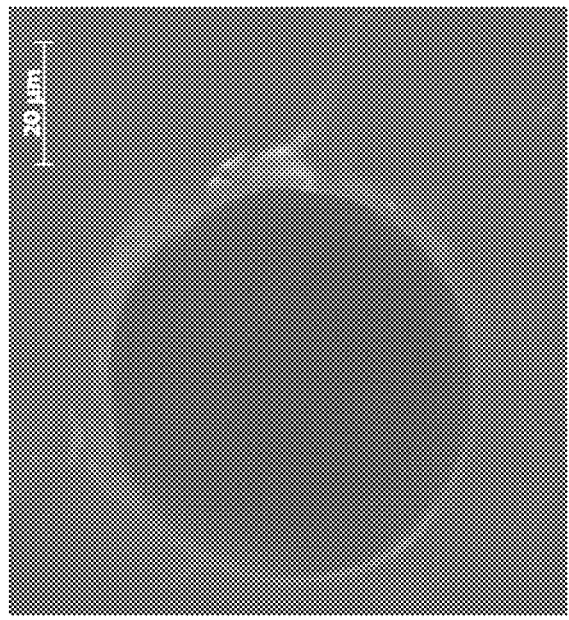

A miniaturized agarose phantom was used to demonstrate the delivery of PRINT® nanoparticles using iontophoresis. A 2% agarose gel was poured into a small test tube (diameter 13 mm) and a capillary tube (o.d. 1 mm) was used to create a central reservoir. An aqueous solution of fluorescent polyampholyte PRINT® nanoparticles (size: 343 nm, charge: ~59 mV, concentration: 9.5 mg/mL) was deposited into the reservoir. A platinum wire (diameter 0.25 mm) was inserted into the reservoir as anode and a similar wire served as a cathode outside the phantom. The phantom was then immersed in a solution of 0.25×PBS, and the electrodes were hooked up to a DC power source using alligator clips. In the negative control, the particles were allowed to passively diffuse into the gel without the application of current for 5 minutes. For iontophoretic delivery, the nanoparticles were driven into the gel by a constant current of 5 mA for the same duration. The phantoms were then cut into 1 mm thick transverse slices that were placed onto glass slides for imaging under a fluorescent microscope. The difference in the extent of migration due to the electric field is shown in FIGS. 31A and 31B. FIG. 31A represents passive diffusion, while FIG. 31B shows results from migration in the 5 mA current.

The following examples, which are not meant to be limiting, generally relate to proof-of-concept studies relating to electric field assisted delivery (EFAD), engineering of EFAD devices, exploratory studies in large animals have been performed, and methods of pharmacokinetic analysis for local delivery mechanisms have been developed. Proof-of-concept studies for EFAD were performed in tumor tissue surrogates and pancreatic tumor tissue. Two EFAD devices were designed and prototyped for different approaches to the primary pancreatic tumor, including endoductal, and surgically implantable. Four large animal models were evaluated for the different device approaches, and the canine model was chosen as the most amenable to all device approaches. A tissue sampling system and methods of pharmacokinetic analysis for tissue and plasma have also been developed. Overall, these devices could potentially offer an entirely new modality for the treatment of pancreatic cancer under the emerging field of interventional oncology. Moreover, the further development of these devices could translate directly into new treatments for other types of primary tumors and metastatic diseases.

Figure 32B:
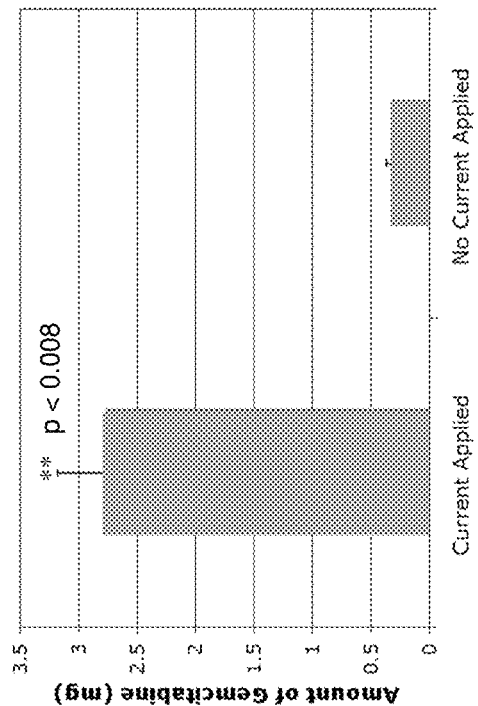
FIG. 32B shows results of an evaluation of the experimental implementation of FIG. 32A according to one aspect of the present disclosure.
Figure 32A:
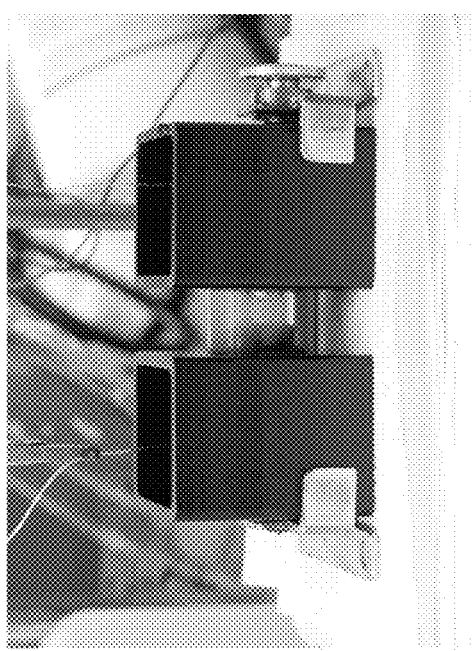
FIG. 32A illustrates an experimental implementation of a delivery system in accordance with one aspect of the present disclosure.

Example 16: Examination of Gemcitabine Transport in Pancreatic Tissue and Tumor Tissue To assess and optimize the electrical transport parameters in tissue, a transport testing system was built (see FIG. 32A). The transport of gemcitabine, the current standard-of-care therapy for pancreatic cancer, was evaluated in orthotopic xenograft tumors using this transport testing system (see FIG. 32B). The tumors chosen for the studies were 1.25 to 1.5 cm in diameter because of compatibility with the size of the transport cell. The gemcitabine was used according to the current clinical formulation (Gemzar® to Eli Lilly and Company), at a concentration relevant to that administered in the clinic. For three tumors, a constant current of 20 mA was applied for 20 minutes, and the amount of gemcitabine was evaluated using a high-performance liquid chromatography (HPLC) analysis method. For three additional tumors, no current was applied, which allowed for passive diffusion of the gemcitabine into the tumor, and the amount of gemcitabine was evaluated using the same HPLC analysis method. As shown in FIG. 32B, an eight-fold increase in the amount of gemcitabine was measured within an orthotopic xenograft tumor when a constant current of 20 mA was applied for 20 minutes compared to the control (no current applied).

Example 17: Implantable Device

The laparoscopic implantable device was developed for surgical implantation onto the surface of the pancreas in proximity to the tumor. The device would be sutured or bioadhered to the pancreas. As seen in FIGS. 33A-D, the laparoscopic implantable system was designed with a drug reservoir, cellulose membrane, polyurethane shell, AgCl electrode, conducting wire, and an inlet and outlet for drug flow into and out of the reservoir. The reservoir is covered by a semi-permeable membrane through which drug can be transported. Drug flows through an inlet tube and is removed from the reservoir through an outlet tube. A metallic electrode is situated at the back of the reservoir. A conducting wire is situated through the reservoir to connect to the metallic electrode. There exist anchor points on the device situated for attachment to tissue. The reservoir and flow system allow for a constant drug concentration around the electrode and the removal of the by-products of the redox reaction. The cellulose membrane will minimize uncontrolled drug flow out of the system.

Example 18: Studies in Large Animals

As there are no readily available large animal models of pancreatic cancer, device development and evaluation will be performed in healthy large animals. Four large animal models, including goats, sheep, dogs, and pigs, were evaluated for three device approaches to the pancreas. Table 1 shows the relative assessment of each animal model. The dog was determined to be the most amenable to all device approaches.

TABLE 1

Assessment of animal model for device approach.
Scale: (1) Not feasible-(5) Very feasible

| Animal | Surgical | Endoscopic | Intravascular |
|---|---|---|---|
| Goat | 2 | 2 | 5 |
| Sheep | 2 | 2 | 5 |
| Dog | 4 | 4 | 4 |
| Pig | 2 | 2 | 4 |

The reservoir based system similar to that shown in FIGS. 33A-D was surgically implanted onto the pancreas of a canine. All animal models were anesthetized and attached to a respirator for the entirety of the study. The implantable device approach was assessed via a laparotomy. The pancreas was assessed for ease of access.

Figure 34:
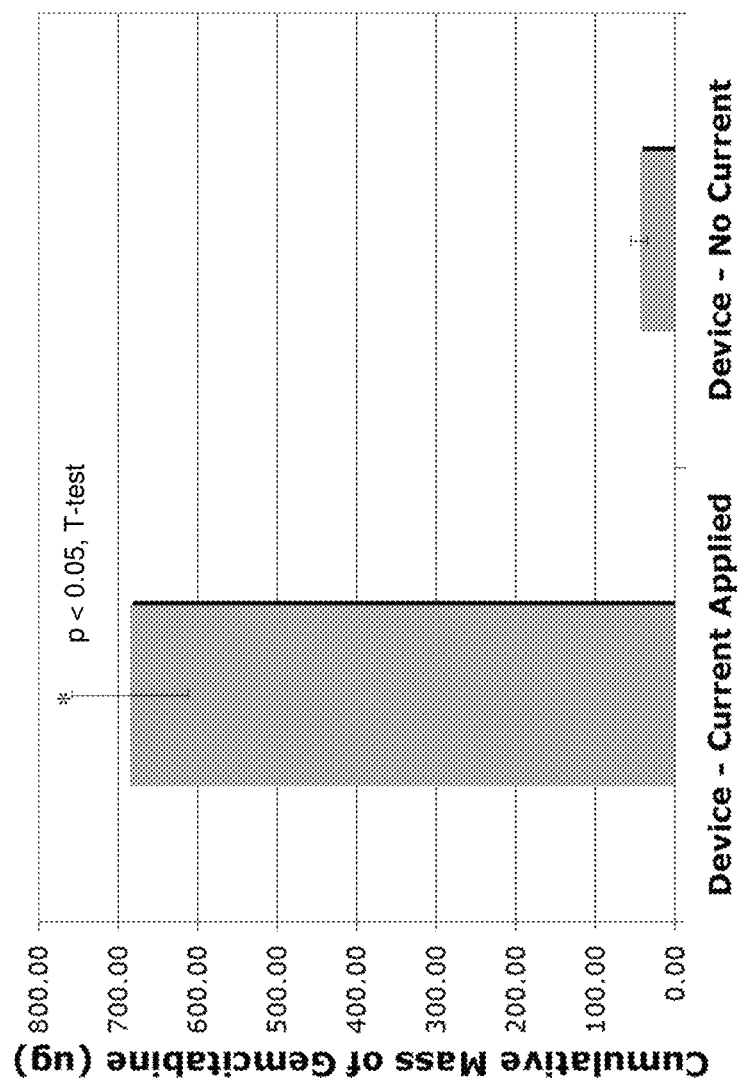
FIG. 34 shows experimental results of an evaluation of an experimental implementation according to one aspect of the present disclosure.

There were three arms for the large animal experiment: 1. Device with current; 2. Device without current; and 3. IV Infusion (see Table 2). The device was sutured onto the right lobe of the canine pancreas. Gemcitabine formulated at clinically relevant concentrations was pumped into and out of the device at ~1.5 mL/min during the application of 10 mA of current applied for 60 minutes. Control experiments were run without current. After administration of therapy, the pancreas was excised and snap frozen for analysis. The gemcitabine was measured from the section tissue using UV-HPLC from established protocols in the literature (see Olive, K P, et al. Science 324 (2009) 1457-1461 and Kirstein M N, et al., J Chromatogr B Analyt Technol Biomed Life Sci. 835 (2006) 136-142). Shown in FIG. 34 are the results obtained from the three experimental arms analyzing the mass of gemcitabine from the entire pancreas.

TABLE 2

Experimental arm parameters

| | Device w/Current | Device w/o Current | IV Infusion |
|---|---|---|---|
| Current | 10 mA | 0 mA | — |
| Time of Administration | 60 minutes | 60 minutes | 30 minutes |
| Sample Size | 5 | 5 | 4 |

Figure 35:
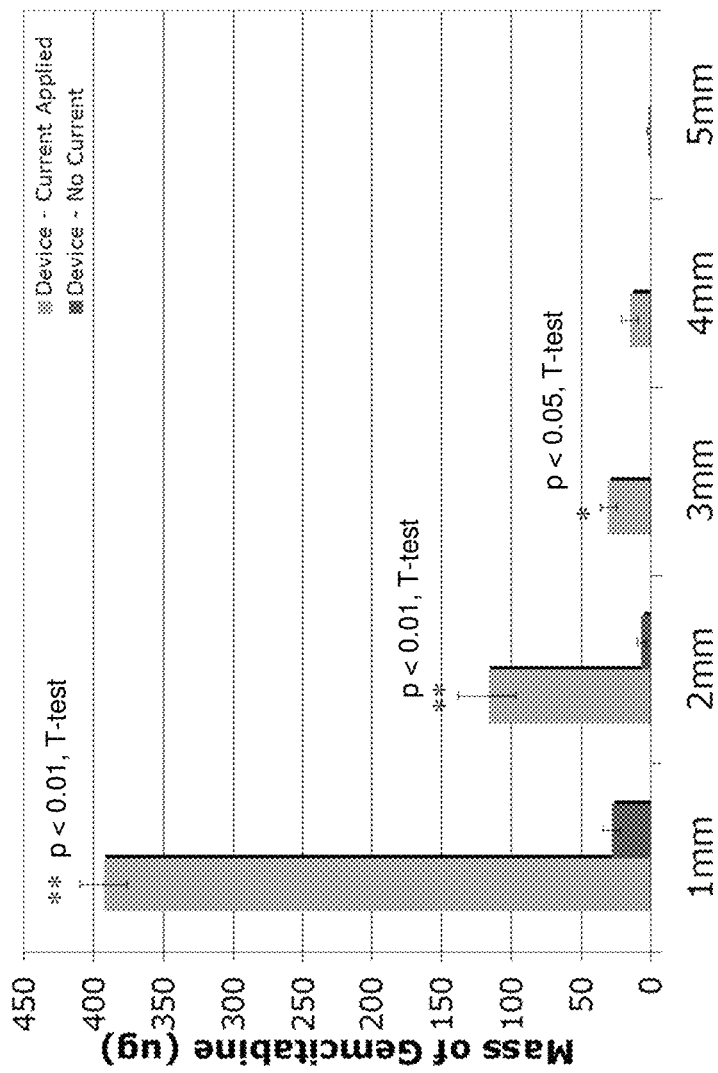
FIG. 35 illustrates experimental results of an evaluation of an experimental implementation according to one aspect of the present disclosure.

In FIG. 35, the transport distance of the gemcitabine is shown for the with and without current arms. In particular, FIG. 35 shows the quantification of gemcitabine mass at different distances away from the electrode. The plasma concentrations determined for the with and without current arms are given in Table 3. Plasma concentrations of gemcitabine were detected at 15-minute increments prior to and during the large animal study. The tissue was sectioned using a cryostat microtome and gemcitabine was extracted using an established extraction method (see Olive et al.). The gemcitabine was detected and quantified using UV-HPLC (see Olive et al. and Kirstein et al.). Essentially, the gemcitabine levels detected in the plasma of the dogs was below the detectable limit.

TABLE 3

Plasma Concentrations of Gemcitabine.

| Sample | Device - Current Applied Gem Concentration (ug/mL) | Device - No Current Gem Concentration (ug/mL) |
|---|---|---|
| −15 min | * | * |
| 0 min | * | * |
| 15 min | * | * |
| 30 min | * | * |
| 45 min | * | * |
| 60 min | * | * |

* Below limit of detection

Pharmacokinetics and Analysis in Tissue and Serum

The pharmacokinetic analysis for tissue and serum has been developed according to a method developed by Kirstein et al. A validated standard curve has been developed and will be used for future in vivo studies (data not shown).

Example 19: Endoductal Device

Figure 36:
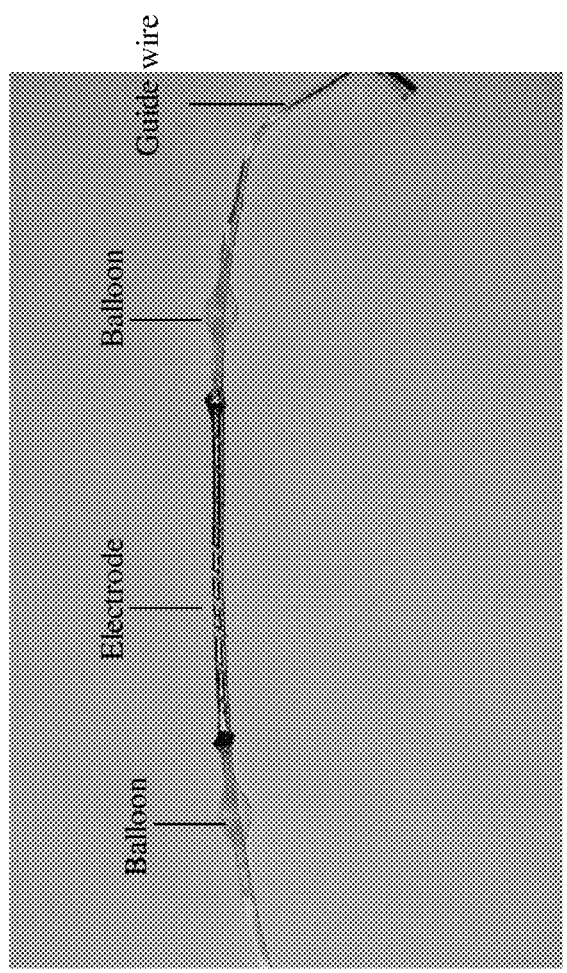
FIG. 36 is an image illustrating an experimental implementation of a delivery system in accordance with an additional aspect of the present disclosure.

A second device approach developed for the treatment of pancreatic cancer was an endoductal device. The device was modeled in a 3D CAD program (SolidWorks® to Dassault Systèmes SolidWorks Corporation) prior to prototyping. The endoductal approach was developed according to endoscopic retrograde cholangiopancreatography (ERCP) devices, which use a duodenoscope to access the major duodenal papilla. A double balloon catheter was designed, as seen in FIG. 36. A multi-luminal tube was used for independent control of balloons, drug expulsion, and electrical contact with the electrode. The catheter contains two independently controlled balloons that sandwich an electrode. The balloons and electrode are UV-cured to the tube. A guide wire is attached to the front end of the device. Drug can be expelled from the device around the electrode and would fill the cavity between the two independently controlled balloons. A conducting wire is in contact with the silver electrode.

Figure 37:
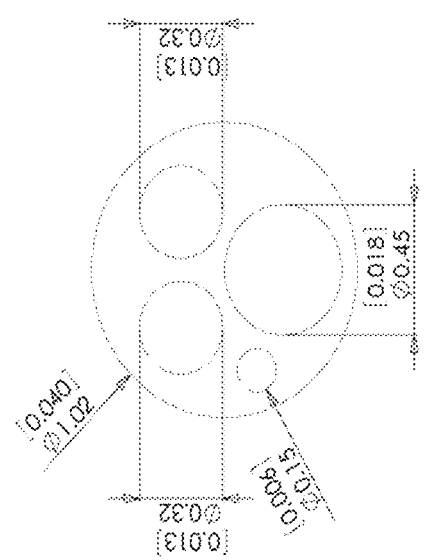
FIG. 37 depicts exemplary dimensions of an experimental implementation of a delivery system in accordance with one aspect of the present disclosure.

The tubing of the catheter contained four lumens for saline, drug, and a conducting wire (see FIG. 37). The two identical lumens were used to inflate the balloons with saline, the small lumens were used for the conducting wire, and the larger lumen was used for the transport of drug. FIG. 37 illustrates exemplary dimensions for the catheter and lumens according to one experimental implementation and is not meant to be limiting. A nitinol conducting wire was connected to a silver electrode located between two prefashioned urethane balloons. The double balloon catheter system created a reservoir for drug containment, which could limit drug exposure to the epithelium; allow for good electrical contact between the electrode and drug, and reduce the effect of extraneous ions in the system. Ultimately, an endoductal EFAD device could be designed to slip over a guide wire that has entered the main pancreatic duct.

What is claimed is:

1. A delivery system for local drug delivery through a target site of internal body tissue, the delivery system comprising:
   a source electrode;
   a counter electrode in electrical communication with the source electrode, the counter electrode being configured to cooperate with the source electrode to form a localized electric field at the target site;
   a cargo capable of being delivered by iontophoresis into the tissue of the target site when exposed to the localized electric field formed between the source electrode and the counter electrode;
   a surgically implantable housing comprising the source electrode and adapted to be secured to the target site, wherein the housing defines a reservoir to carry the cargo; and
   a semi-permeable membrane sealing the reservoir for containing the cargo,
   wherein the localized electric field formed between the source electrode and the counter electrode induces the cargo to permeate the membrane and transports the cargo through the membrane into the tissue; and
   means for securing the housing to the tissue of the target site,
wherein the counter electrode is spaced from the housing and the source electrode, such that the source electrode and counter electrode are configured to receive tissue of the target site therebetween.

2. The delivery system as recited in claim 1, wherein the housing defines an inlet and an outlet to the reservoir for flow of cargo into and out of the reservoir.

3. The delivery system as recited in claim 1, wherein the cargo comprises at least one of nucleic acids, proteins, organic nanoparticles, therapeutic agents, and imaging agents.

4. The delivery system as recited in claim 1, wherein the cargo comprises a therapeutic agent.

5. The delivery system as recited in claim 4, wherein the therapeutic agent comprises gemcitabine.

6. The delivery system as recited in claim 1, wherein the securing means comprises a plurality of anchor points defining suture openings.

7. The delivery system as recited in claim 1, wherein the securing means comprises a biological adhesive.

8. The delivery system as recited in claim 1, further comprising anion selective membrane surrounding the counter electrode.

9. The delivery system as recited in claim 1, further comprising an electrode deployment device configured to insert at least one of the source electrode and the counter electrode proximate to the target site.

10. The delivery system as recited in claim 1 further comprising a coolant device operably engaged with the counter electrode, the coolant device being configured to provide cooling to the counter electrode.

* * * * *